United States Patent
Nakao et al.

(10) Patent No.: US 11,631,177 B2
(45) Date of Patent: Apr. 18, 2023

(54) MACHINE LEARNING DEVICE, ESTIMATION DEVICE, NON-TRANSITORY COMPUTER READABLE MEDIUM, AND LEARNED MODEL

(71) Applicant: KYOTO UNIVERSITY, Kyoto (JP)

(72) Inventors: Megumi Nakao, Kyoto (JP); Toyofumi Yoshikawa, Kyoto (JP); Junko Tokuno, Kyoto (JP); Hiroshi Date, Kyoto (JP); Tetsuya Matsuda, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 119 days.

(21) Appl. No.: 17/274,065

(22) PCT Filed: Sep. 3, 2019

(86) PCT No.: PCT/JP2019/034558
§ 371 (c)(1),
(2) Date: Mar. 5, 2021

(87) PCT Pub. No.: WO2020/054503
PCT Pub. Date: Mar. 19, 2020

(65) Prior Publication Data
US 2021/0256703 A1    Aug. 19, 2021

(30) Foreign Application Priority Data
Sep. 13, 2018   (JP) .............................. JP2018-171825

(51) Int. Cl.
*G06T 15/00*   (2011.01)
*G06T 7/00*    (2017.01)
(Continued)

(52) U.S. Cl.
CPC ............ *G06T 7/0016* (2013.01); *A61B 34/10* (2016.02); *G06N 3/08* (2013.01); *G06T 7/251* (2017.01);
(Continued)

(58) Field of Classification Search
CPC .......... G06N 3/08; G06N 20/10; G06T 7/248; G06T 2207/10076; G06T 2207/10088;
(Continued)

(56) References Cited

U.S. PATENT DOCUMENTS 10,074,160 B2 * 9/2018 Kim .................... G06T 15/06
11,216,948 B2 * 1/2022 Yang .................... G06T 11/60
(Continued)

FOREIGN PATENT DOCUMENTS

JP    2008200482 A    9/2008
JP    2015130972 A    7/2015
(Continued)

OTHER PUBLICATIONS

Eppenhof KA, Pluim JP. Pulmonary CT Registration Through Supervised Learning With Convolutional Neural Networks. IEEE Transactions on Medical Imaging. Oct. 26, 2018;38(5):1097-105.*
(Continued)

*Primary Examiner* — Phu K Nguyen
(74) *Attorney, Agent, or Firm* — Oliff PLC

(57) ABSTRACT

A machine learning device includes: a generation unit generating a first shape model representing a shape of an object before deformation and a second shape model representing a shape of the object after the deformation based on measurement data before and after the deformation; and a learning unit learning a feature amount including a difference value between each micro region and another micro region that constitute the first shape model, and a relation providing a displacement from the each micro region of the
(Continued)

first shape model to each corresponding micro region of the second shape model.

18 Claims, 41 Drawing Sheets

(51) Int. Cl.

| | | |
|---|---|---|
| A61B 34/10 | (2016.01) | |
| G06T 7/50 | (2017.01) | |
| G06T 7/73 | (2017.01) | |
| G06T 7/246 | (2017.01) | |
| G16H 30/20 | (2018.01) | |
| G06N 3/08 | (2023.01) | |
| G06T 17/20 | (2006.01) | |

(52) U.S. Cl.
CPC ............... *G06T 7/50* (2017.01); *G06T 7/75* (2017.01); *G06T 17/20* (2013.01); *G16H 30/20* (2018.01); *A61B 2034/105* (2016.02); *G06T 2207/20081* (2013.01); *G06T 2207/30061* (2013.01)

(58) Field of Classification Search
CPC . G06T 2207/10116; G06T 2207/30061; G06T 2207/20081; G06T 2210/41; G06T 2207/30064; G06T 7/0016; G06T 2207/20084; G06T 7/75; G06T 7/50; G06T 7/251; G06T 2200/04; G06T 2207/10081; G06T 2207/10068; G06T 2207/10104; G06T 17/20; A61B 2034/105; A61B 34/10; G16H 30/20; G16H 30/40; G16H 50/20
USPC .......................................................... 345/418
See application file for complete search history.

(56) References Cited

U.S. PATENT DOCUMENTS

| | | |
|---|---|---|
| 2008/0144939 A1 | 6/2008 | Russakoff |
| 2016/0314587 A1 | 10/2016 | Ishikawa et al. |
| 2016/0364880 A1 | 12/2016 | Barratt et al. |
| 2018/0095450 A1* | 4/2018 | Lappas .................. B33Y 10/00 |
| 2018/0161099 A1 | 6/2018 | Dumenil et al. |
| 2020/0302187 A1* | 9/2020 | Wang .................. H04L 25/0224 |

FOREIGN PATENT DOCUMENTS

| | | |
|---|---|---|
| JP | 2017512522 A | 5/2017 |
| JP | 2018522695 A | 8/2018 |

OTHER PUBLICATIONS

Eppenhof KA, Lafarge MW, Moeskops P. Veta M, Pluim JP. Deformable image registration using convolutional neural networks. In2018 SPIE Medical Imaging: Image Processing Mar. 15, 2018 (p. 105740S). SPIE.*
Wu S, Nakao M, Tokuno J, Chen-Yoshikawa T, Matsuda T. Reconstructing 3D lung shape from a single 2D image during the deaeration deformation process using model-based data augmentation. In2019 IEEE EMBS International Conference on Biomedical & Health Informatics (BHI) May 19, 2019 (pp. 1-4). IEEE.*
Nov. 26, 2019 International Search Report issued in International Patent Application No. PCT/JP2019/034558.
M. Nakao, et al., "Direct Volume Manipulation for Visualizing Intraoperative Liver Resection Process", Computer Methods and Programs in Biomedicine, vol. 113, No. 3, pp. 1-10, Mar. 2014.
J. Yamamoto, et al., "Estimation of elastic deformation by partial observation with kernel method", Transactions of the Japanese Society for Medical and Biological Engineering, p. 180, 2017.
H. Fan et al., "A point set generation network for 3D object reconstruction from a single image," CVPR, 2017, pp. 305-613.
May 11, 2022 Extended European Search Report issued in Patent Application No. 19859716.3.
Shi, Yonghong et al., "Learning statistical correlation for fast prostate registration in image-guided radiotherapy", Medical Physics, AIP, (2011), vol. 38, No. 11, pp. 5980-5991.
Lorente, D et al., "A framework for modelling the biomechanical behaviour of the human liver during breathing in real time using machine learning", Expert Systems with Applications, (2016), vol. 71, pp. 342-357.
Morooka, Ken'ichi et al., "A Survey on Statistical Modeling and Machine Learning Approaches to Computer Assisted Medical Intervention: Intraoperative Anatomy Modeling and Optimization of Interventional Procedures", IEICE Transactions on Information and Systems, (2013), vol. E96.D, No. 4, pp. 784-797.

* cited by examiner

× BEFORE ROTATION
○ AFTER ROTATION
● REPOSITION BY UPSAMPLING

INPUT $x_i$ : FEATURE AMOUNT DATA $x_i$ PER EACH VERTEX i
OF SHAPE MODEL BEFORE DEFORMATOPM
OUTPUT $y_i$ : DISPLACEMENT AMOUNT DATA DUE TO DEFORMATION
FUNCTION $f$ : INPUT/OUTPUT RELATION TO BE LEARNED

CORRESPONDING VERTEX $i'$ AFTER DEFORMATION

FIG.20

| REGRESSION MODEL | SUPERIOR LOBE [mm] | INFERIOR LOBE [mm] |
|---|---|---|
| MULTIPLE LINEAR REGRESSION MODEL | 8.8±3.3 | 10.1±5.4 |
| LASSO REGRESSION MODEL | 9.1±3.4 | 9.9±5.0 |
| KERNEL REGRESSION MODEL | 3.1±0.9 | 3.9±1.9 |

FIG.21

| FEARTURE AMOUNT GROUP | SUPERIOR LOBE [mm] | INFERIOR LOBE [mm] |
|---|---|---|
| FEARTURE AMOUNT GROUP 1 | 3.1±0.9 | 3.9±1.9 |
| FEARTURE AMOUNT GROUP 2 | 3.1±0.9 | 3.9±1.9 |
| FEARTURE AMOUNT GROUP 3 | 3.2±1.5 | 5.3±4.9 |
| FEARTURE AMOUNT GROUP 4 | 11.1±3.5 | 12.1±6.2 |

● FEARTURE AMOUNT GROUP 1 : ($v_i, n_i, l_i, d_{ij}, s_i, r_i$)

● FEARTURE AMOUNT GROUP 2 : ($d_{ij}$)

● FEARTURE AMOUNT GROUP 3 : ($d_{ij}, n_i \times 100$)

● FEARTURE AMOUNT GROUP 4 : ($v_i, n_i, l_i, s_i, r_i$)

FIG.22

| SPECIMEN | SUPERIOR LOBE [mm]] | INFERIOR LOBE [mm] |
|---|---|---|
| 1 | 2.2 | 1.3 |
| 2 | 5 | 6.7 |
| 3 | 3.2 | 2.5 |
| 4 | 1.8 | 4.6 |
| 5 | 1.7 | 2.8 |
| 6 | 3.2 | 4 |
| 7 | 1.8 | 3.9 |
| 8 | 2.4 | 6.4 |
| 9 | 1.5 | 3 |
| 10 | 1.9 | 2.9 |
| 11 | 3.7 | 2.4 |

AVERAGE SHAPE MODEL

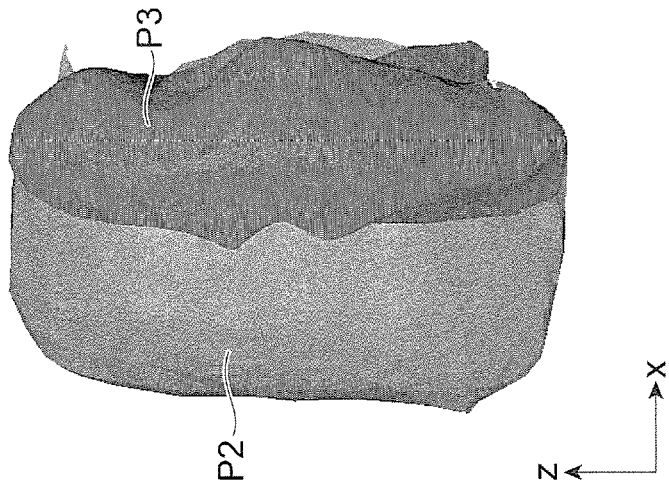
FIG.34A  FIG.34B  FIG.34C
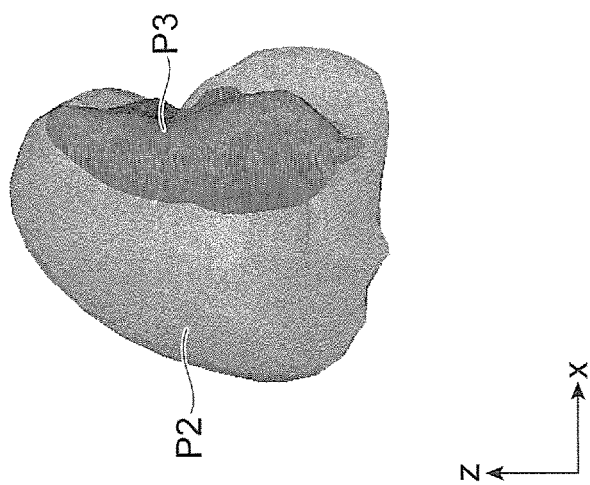
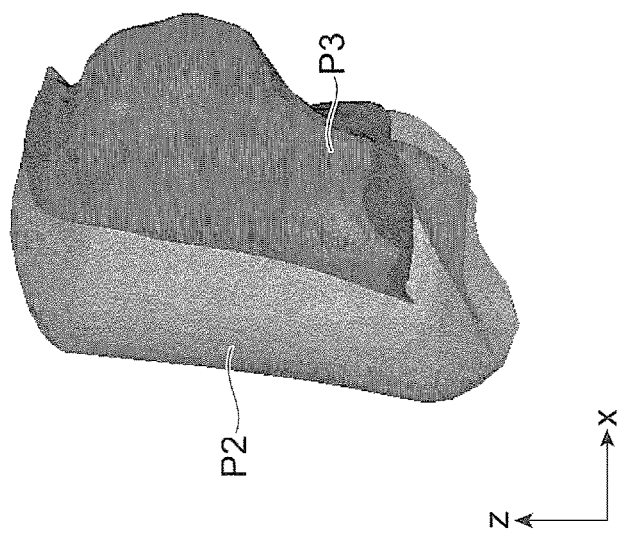
FIG.34D
| SPECIMEN | MD[mm] | HD[mm] | DSC[%] |
|---|---|---|---|
| A | 0.21 | 0.98 | 98.93 |
| B | 0.15 | 0.79 | 99.24 |
| C | 0.23 | 1.30 | 98.94 |

FIG.35

| SPECIMEN | MD[mm] | HD[mm] | DSC[%] |
|---|---|---|---|
| A | 0.33 | 1.91 | 98.14 |
| B | 0.54 | 2.26 | 97.94 |
| C | 0.39 | 1.53 | 98.31 |

FIG.38A  FIG.38B  FIG.38C
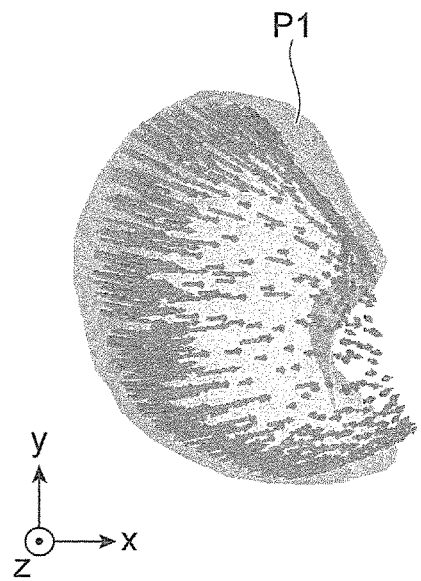
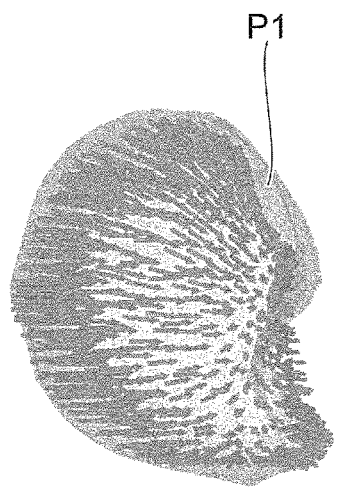
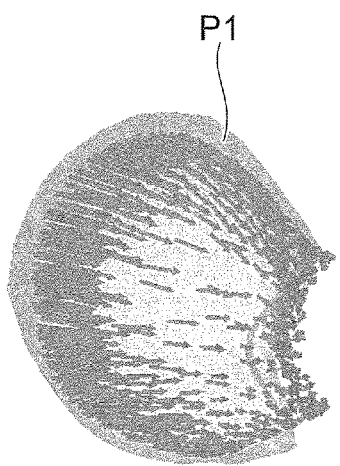
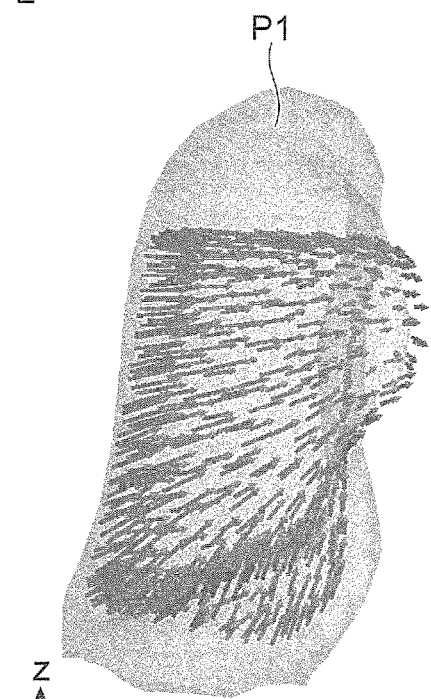
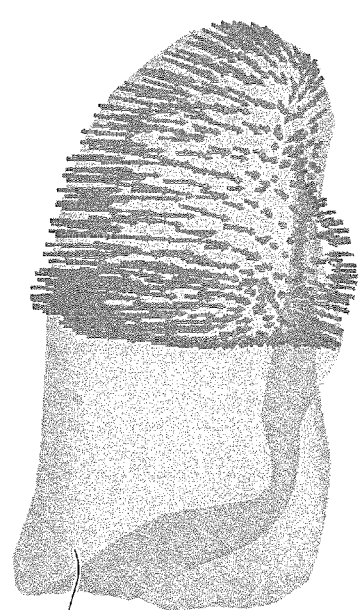
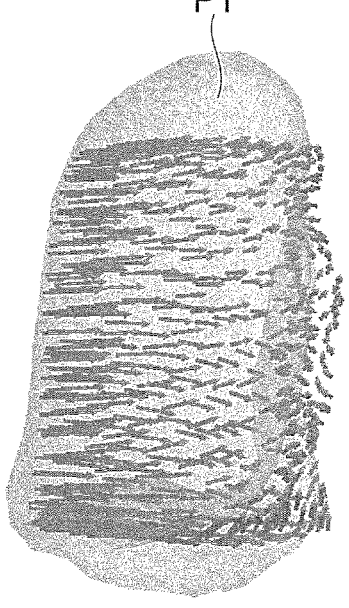
P1    CT IMAGE CAPTUTURED BEFORE SURGERY (ENTIRE LUNG IS IN AERATED CONDITION)
⟶ DISPLACEMENT AMOUN DATA $y_i$ FIG.39A
FIG.39B
FIG.39C
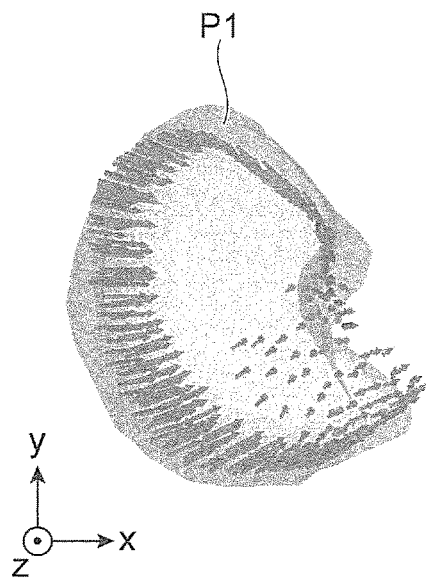
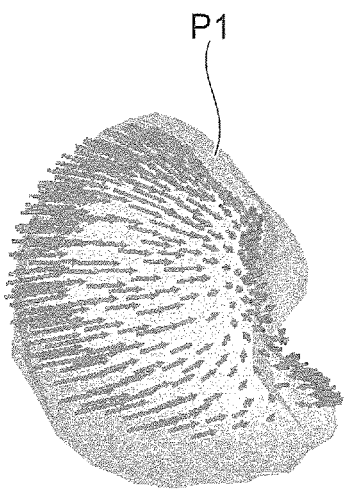
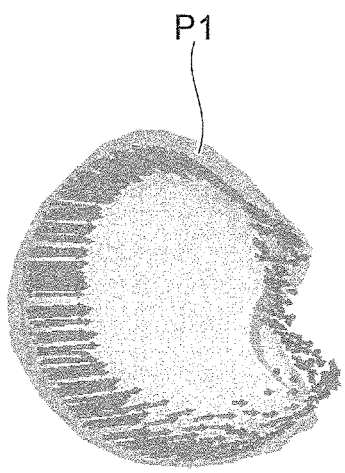
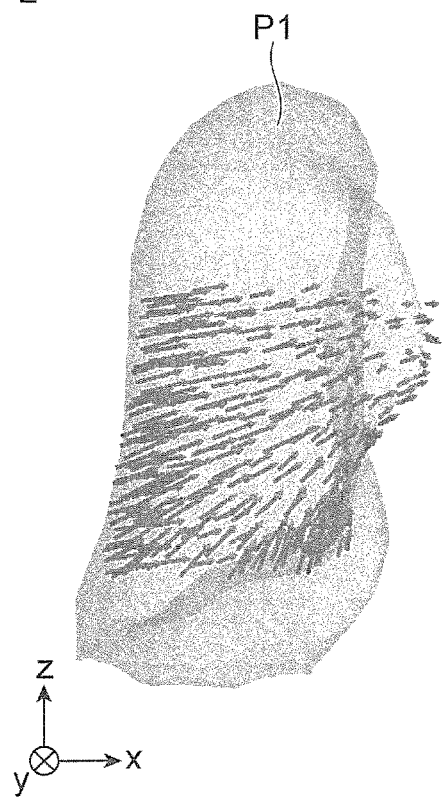
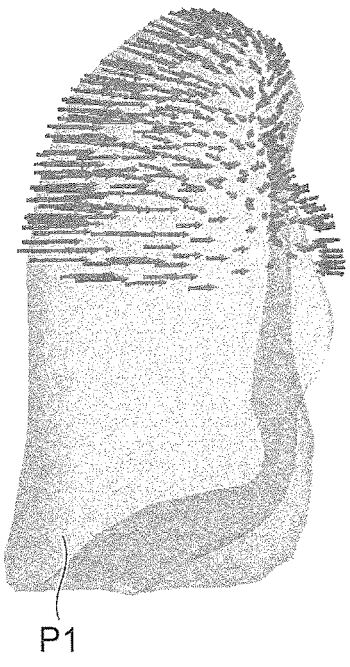
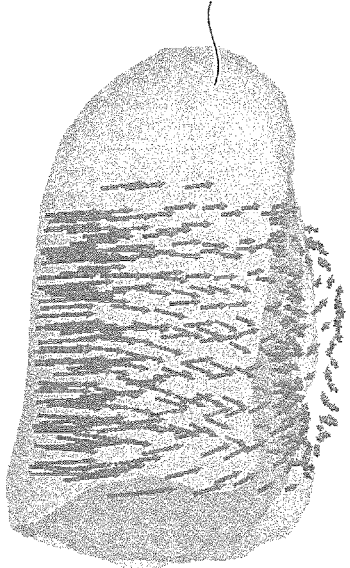
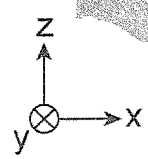 P1    CT IMAGE CAPTUTURED BEFORE SURGERY (ENTIRE LUNG IS IN AERATED CONDITION)
⟶ DISPLACEMENT AMOUN DATA $y_i$ PS — POST-DEFORMATION SHAPE ESTIMATED BY USE OF LEARNED MODEL
P1 — CT IMAGE CAPTUTURED BEFORE SURGERY (ENTIRE LUNG IS IN AERATED CONDITION)

MACHINE LEARNING DEVICE, ESTIMATION DEVICE, NON-TRANSITORY COMPUTER READABLE MEDIUM, AND LEARNED MODEL

TECHNICAL FIELD

The present invention relates to a machine learning device, an estimation device, a non-transitory computer readable medium, and a learned model.

BACKGROUND ART

Advances in imaging techniques have increased the chance of early detection of micropulmonary nodules and thoracoscopic surgery has been widely performed. However, the lungs are in aerated conditions prior to surgery, while being in deaerated conditions during surgery, which results in significant deformation of the lungs. As a result, the nodules position during surgery changes from the nodules position identified prior to the surgery. To counteract this change, there exists a technique to identify positions of multiple micronodules by registering sites of dyes marked prior to surgery with Computed Tomography (CT) images captured during the surgery.

In addition, examples of a method without using the CT capturing during surgery include simulation of organ deformation (Non-Patent Document 1) or simulation of organ deformation using a model that learned deformation of an elastic body due to tension (Non-Patent Document 2).

CITATION LIST

Non-Patent Literature

Non-Patent Document 1
M. Nakao, Y. Oda, K. Taura, and K. Minato, Direct Volume Manipulation for Visualizing Intraoperative Liver Resection Process, Computer Methods and Programs in Biomedicine, Vol. 113, No. 3, pp. 725-735, March 2014.
Non-Patent Document 2
U. Yamamoto, M. Nakao, M. Ohzeki, and T. Matsuda, Estimation of elastic deformation by partial observation with kernel method, Transactions of the Japanese Society for Medical and Biological Engineering, p. 180, 2017.

SUMMARY OF INVENTION

Technical Problem

However, the method of registering the sites of dyes marked prior to surgery with CT images captured during the surgery has increased the burden on both doctors and patients, including the need for additional measurements.

In addition, the method described in Non-Patent Document 1 has a problem in which it is difficult to actually measure mechanical properties and physical conditions specific to each patient. The method described in Non-Patent Document 2 only simulates the deformation of the artificial data generated by simulation.

An object of the present invention is to generate a learned model with high estimation accuracy compared to a case of learning deformation with a unit of an entire shape.

Solution to Problem

The invention described in claim 1 provides a machine learning device including: a generation unit generating a first shape model representing a shape of an object before deformation and a second shape model representing a shape of the object after the deformation based on measurement data before and after the deformation; and a learning unit learning a feature amount including a difference value between each micro region and another micro region that constitute the first shape model, and a relation providing a displacement from the each micro region of the first shape model to each corresponding micro region of the second shape model.

The invention described in claim 2 provides the machine learning device according to claim 1, wherein, when the generation unit generates a third shape model with a change in positions of vertexes, which are elements of the first shape model, and a fourth shape model with a change in positions of vertexes, which are elements of the second shape model, the learning unit also learns a feature amount including a difference value between each micro region and another micro region that constitute the third shape model, and a relation providing a displacement from the each micro region of the third shape model to each corresponding micro region of the fourth shape model.

The invention described in claim 3 provides the machine learning device according to claim 1, wherein the feature amount is defined by at least one of coordinates giving each micro region, a gradient or a normal vector defining each micro region, a curvature defining each micro region, Voronoi area of each micro region, a shrinkage ratio of each micro region, and a deviation amount between each micro region and a corresponding region of an average shape model.

The invention described in claim 4 provides the machine learning device according to claim 1, wherein the difference value giving the feature amount is calculated with the micro regions of at least 5% of total micro regions constituting the first shape model.

The invention described in claim 5 provides the machine learning device according to claim 1 or 2, wherein the learning unit learns the relation by using a kernel regression model.

The invention described in claim 6 provides the machine learning device according to claim 1 or 2, wherein the measurement data before and after the deformation is medical image data.

The invention described in claim 7 provides the machine learning device according to claim 6, wherein the deformation is deaerated deformation of a lung, medical image data of a lung of a patient having treated pneumothorax is used as the measurement data before the deformation due to deaeration, and medical image data of the lung of the patient before treatment of pneumothorax is used as the measurement data after the deformation due to deaeration.

The invention described in claim 8 provides the machine learning device according to claim 6, wherein the deformation includes deformation of an organ or movement of a position of an organ due to breathing, time variation, or differences in specimens.

The invention described in claim 9 provides the machine learning device according to claim 1, wherein the first shape model and the second shape model are three-dimensional vertex models.

The invention described in claim 10 provides a non-transitory computer readable medium storing a program causing a computer to execute: a function of generating a first shape model representing a shape of an object before deformation and a second shape model representing a shape of the object after the deformation based on measurement data before and after the deformation; and a function of learning a feature amount including a difference value between each micro region and another micro region of the first shape model, and a relation providing a displacement from the each micro region of the first shape model to each corresponding micro region of the second shape model.

The invention described in claim 11 provides an estimation device including: an estimation unit, when any measurement data is given, using a learned model having learned a feature amount including a difference value between each micro region and another micro region in a first shape model generated from measurement data before deformation, and a relation providing a displacement from the each micro region of the first shape model to each corresponding micro region of a second shape model after the deformation, to thereby estimate a shape after the deformation corresponding to the any measurement data.

The invention described in claim 12 provides the estimation device according to claim 11, wherein the estimation unit calculates a feature amount including a difference value between a micro region and another micro region of a shape model generated for the inputted measurement data, and estimates a displacement of a feature amount corresponding to each micro region by interpolating a relation stored in the learned model.

The invention described in claim 13 provides a non-transitory computer readable medium storing a program causing a computer to execute: a function of, when any measurement data is given, using a learned model having learned a feature amount including a difference value between each micro region and another micro region in a first shape model generated from measurement data before deformation, and a relation providing a displacement from the each micro region of the first shape model to each corresponding micro region of a second shape model after the deformation, to thereby estimate a shape after the deformation corresponding to the any measurement data.

The invention described in claim 14 provides a learned model causing a computer to execute a function including: providing a relation having a feature amount including a difference value between each micro region and another micro region in a first shape model generated from measurement data before deformation as an input, and a displacement from the each micro region of the first shape model to each corresponding micro region of a second shape model after the deformation as an output, and, when any measurement data is given, computing a displacement corresponding to each micro region of a shape model corresponding to the any measurement data by using the relation, to thereby estimate a shape after the deformation corresponding to the any measurement data.

The invention described in claim 15 provides a machine learning device including: a generation unit generating shape models representing individual shapes of a first object and an average shape model based on plural measurement data items of the first object; and a learning unit learning a distribution of a feature amount including a difference value between each micro region constituting the shape model representing the individual shape and each corresponding micro region of the average shape model, and a relation between a distribution of the difference value and a region where a second object having a constraint relation with the first object exists.

The invention described in claim 16 provides the machine learning device according to claim 15, wherein the constraint relation includes a relation in which the second object is adjacent to or connected to the first object.

The invention described in claim 17 provides a non-transitory computer readable medium storing a program causing a computer to execute: a function of generating shape models representing individual shapes of a first object and an average shape model based on plural measurement data items of the first object; and a function of learning a distribution of a feature amount including a difference value between each micro region constituting the shape model representing the individual shape and each corresponding micro region of the average shape model, and a relation between a distribution of the difference value and a region where a second object having a constraint relation with the first object exists.

Advantageous Effects of Invention

According to the invention described in claim 1, it is possible to generate a learned model with high estimation accuracy compared to a case of learning deformation with a unit of an entire shape.

According to the invention described in claim 2, it is possible to generate the learned model with high estimation accuracy in spite of the number of measurement data items.

According to the invention described in claim 3, it is possible to generate a learned model with high estimation accuracy compared to a case of learning deformation with a unit of an entire shape.

According to the invention described in claim 4, it is possible to generate a learned model with high estimation accuracy even in the case of the small number of micro regions for which difference values are to be obtained.

According to the invention described in claim 5, it is possible to increase estimation accuracy of the learned model even in the case where non-linear relationship is included between inputs and outputs.

According to the invention described in claim 6, it is possible to use the generated learned model in the medical field.

According to the invention described in claim 7, it is possible to generate the learned model capable of estimating the shape of the deaerated lung with high accuracy.

According to the invention described in claim 8, it is possible to use the generated learned model in the medical field.

According to the invention described in claim 9, it is possible to estimate deformation of a three-dimensional shape.

According to the invention described in claim 10, it is possible to cause a computer to operate as a device generating a learned model with high estimation accuracy as compared to a case of learning deformation with a unit of an entire shape.

According to the invention described in claim 11, it is possible to estimate a deformed shape with high accuracy as compared to a case of using a learned model that learned deformation with a unit of an entire shape.

According to the invention described in claim 12, it is possible to estimate a deformed shape with high accuracy as compared to a case of using a learned model that learned deformation with a unit of an entire shape.

According to the invention described in claim 13, it is possible to cause a computer to operate as a device generating a learned model with high estimation accuracy as compared to a case of using a learned model that learned deformation with a unit of an entire shape.

According to the invention described in claim 14, it is possible to provide a learned model capable of estimating a deformed shape with high accuracy as compared to a case using a learned model that learned deformation with a unit of an entire shape.

According to the invention described in claim 15, it is possible to estimate a position of another target object with high accuracy rather than learning the positional relationship between the objects in a constraint relation in the unit of the shape.

According to the invention described in claim 16, it is possible to estimate a position of another target object with high accuracy rather than learning the positional relationship between the objects in a constraint relation in the unit of the shape.

According to the invention described in claim 17, it is possible to estimate a position of another target object with high accuracy rather than learning the positional relationship between the objects in a constraint relation in the unit of the shape.

BRIEF DESCRIPTION OF DRAWINGS

FIG. 4A shows a displacement model A, FIG. 4B shows a displacement model B, and FIG. 4C shows a displacement model C;

FIG. 20 illustrates differences in estimation errors among the three types of regression models;

FIG. 21 illustrates differences in estimation errors among the four types of feature amount data;

FIG. 22 shows the error between the estimation result and the actually measured value for each specimen in the case of using a kernel regression model as the regression model with feature amount data including difference between vertexes;

FIG. 32A shows the CT images of a specimen A, FIG. 32B shows the CT images of a specimen B, and FIG. 32C shows the CT images of a specimen C;

FIGS. 34A to 34D illustrate the results of alignment of the CT image P2 (namely, the partial shape model before deformation) of the lung in the aerated condition captured with the cone-beam CT and the CT image P3 (namely, the partial shape model after deformation) of the same lung in the deaerated condition captured with the cone-beam CT, where FIG. 34A shows the shape model of a specimen A, FIG. 34B shows the shape model of a specimen B, FIG. 34C shows the shape model of a specimen C, and FIG. 34D shows the results of the alignment;

FIG. 35 explains results of alignment of the CT image P1 (pre-deformation shape model) of the lung in the aerated condition of the specimen captured with CT with the template shape T of the lung;

FIG. 37A shows the shape model of a specimen A, and FIG. 37B shows the shape model of a specimen B;

FIGS. 38A to 38C illustrate the displacement amount data $y_i$ in the case where the vertexes near the boundary are not removed, where FIG. 38A shows the displacement amount data $y_i$ that appears in the x-y plane and the displacement amount data $y_i$ that appears in the x-z plane of a specimen A, FIG. 38B shows the displacement amount data $y_i$ that appears in the x-y plane and the displacement amount data $y_i$ that appears in the x-z plane of a specimen B, and FIG. 38C shows the displacement amount data $y_i$ that appears in the x-y plane and the displacement amount data $y_i$ that appears in the x-z plane of a specimen C;

FIGS. 39A to 39C illustrate the displacement amount data $y_i$ in the case where the vertexes near the boundary are removed, where FIG. 39A shows the displacement amount data $y_i$ that appears in the x-y plane and the displacement amount data $y_i$ that appears in the x-z plane of a specimen A, FIG. 39B shows the displacement amount data $y_i$ that appears in the x-y plane and the displacement amount data $y_i$ that appears in the x-z plane of a specimen B, and FIG. 39C shows the displacement amount data $y_i$ that appears in the x-y plane and the displacement amount data $y_i$ that appears in the x-z plane of a specimen C;

FIG. 40A shows the actual surgical image, and FIG. 40B shows the estimated shape PS.

DESCRIPTION OF EMBODIMENTS

Hereinafter, with reference to attached drawings, exemplary embodiments according to the present invention will be described in detail.

Exemplary Embodiment 1

<System Configuration>

Figure 1:
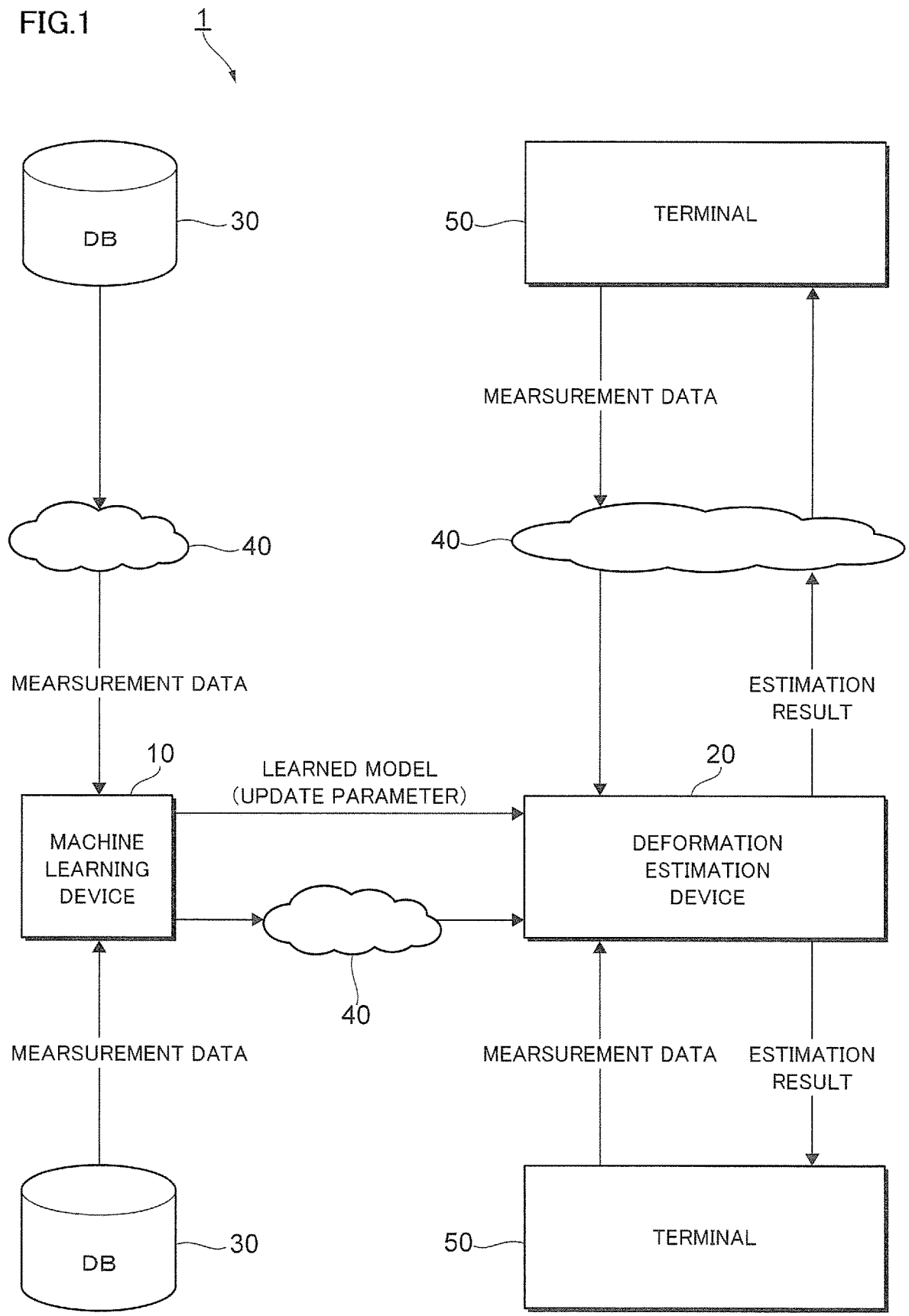
FIG. 1 illustrates a conceptual configuration example of an estimation system that estimates the deformed shape related to any measurement data using a learned model that has learned a relation between the measurement data before and after the deformation.

FIG. 1 illustrates a conceptual configuration example of an estimation system 1 that estimates the deformed shape related to any measurement data using a learned model that has learned a relation between the measurement data before and after the deformation.

The estimation system 1 shown in FIG. 1 includes a machine learning device 10 that generates a learned model from the measurement data as teacher data, and a deformation estimation device 20 that uses the generated learned model to estimate the deformed shape of any measurement data.

In the case of the exemplary embodiment, input of the measurement data to the machine learning device 10 may be performed directly from a database (DB) 30 storing the measurement data, or may be performed via a network 40. The network 40 here may be a local area network or the Internet.

In addition, the generated learned models and the parameters (update parameters) updating the learned models are provided to the deformation estimation device 20 directly or via the network 40. However, the learned models and update parameters may be provided to the deformation estimation device 20 via a not-shown storage medium. The update parameter is the value of the coefficient of the deformation function updated by the learning, for example.

The deformation estimation device 20 inputs the measurement data to be estimated directly from a terminal 50 or via the network 40, and outputs the result of estimation (estimation result) to the terminal 50 directly or via the network 40. The terminal 50 here may be, for example, a surgery support system or a radiotherapy device.

<Machine Learning Device>

Figure 2:
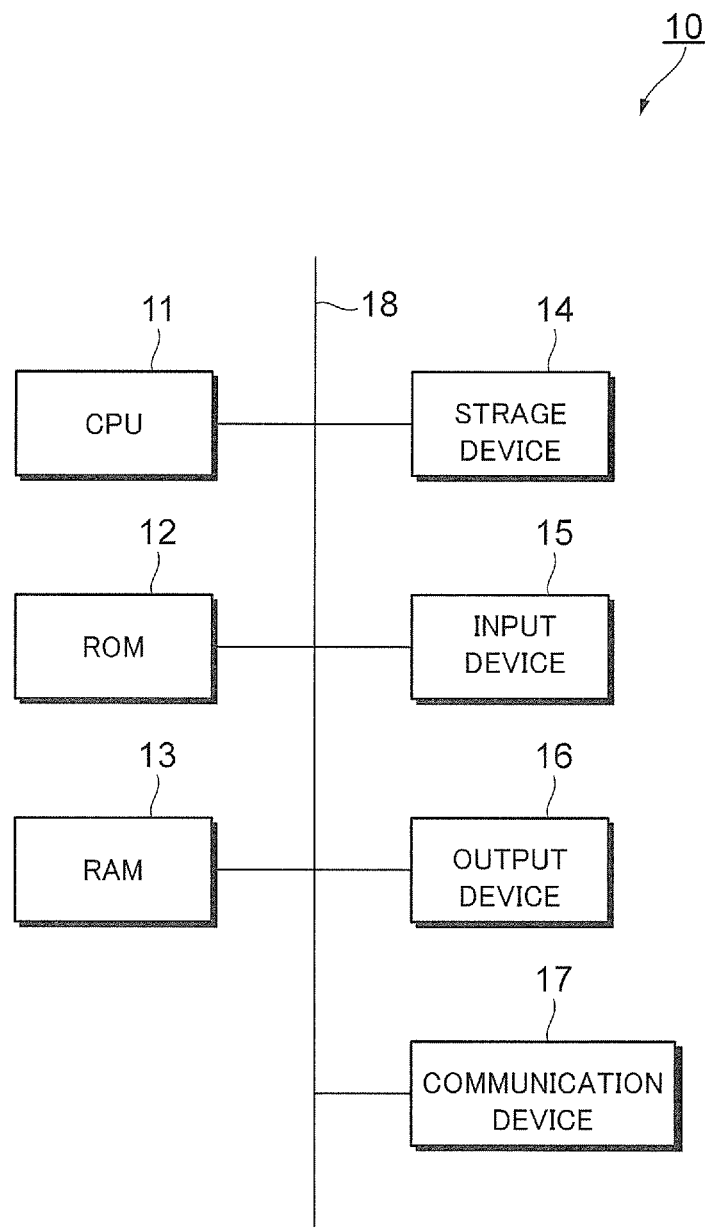
FIG. 2 shows an example of a hardware configuration of a machine learning device.

FIG. 2 shows an example of a hardware configuration of the machine learning device 10.

The machine learning device 10 shown in FIG. 2 includes: a central processing unit (CPU) 11 controlling the entire device through execution of programs (including basic software); a ROM 12 storing programs, such as the basic input output system (BIOS); and a random access memory (RAM) 13 used as execution regions of the programs. The CPU 11, the ROM 12, and the RAM 13 in this case constitute a so-called computer and execute various kinds of information processing. Note that the ROM 12 is configured with a nonvolatile semiconductor memory.

A storage device 14, for example, is configured with a hard disk device, and stores application programs learning the relation between before and after the deformation and the learned models that are the results of the learning. Note that the storage device 14 is not limited to the internal device, but may be an external device, or a networked storage.

An input device 15, for example, is a keyboard or a mouse, and is used for operation inputting. An output device 16 is a display device or a printing device used to display operation screens or to print information. Note that, in the case where the machine learning device 10 is implemented as a server, the input device 15 and the output device 16 may be provided on the not-shown terminal side.

A communication device 17 is used to communicate with external devices. The communication device 17 is used to input measurement data from the database 30 and to output the learned models or the update parameters to the deformation estimation device 20 (including distribution).

The CPU 11 and each component are connected via a bus 18 and not-shown signal wires.

Note that the machine learning device 10 can also be implemented as dedicated hardware.

Figure 3:
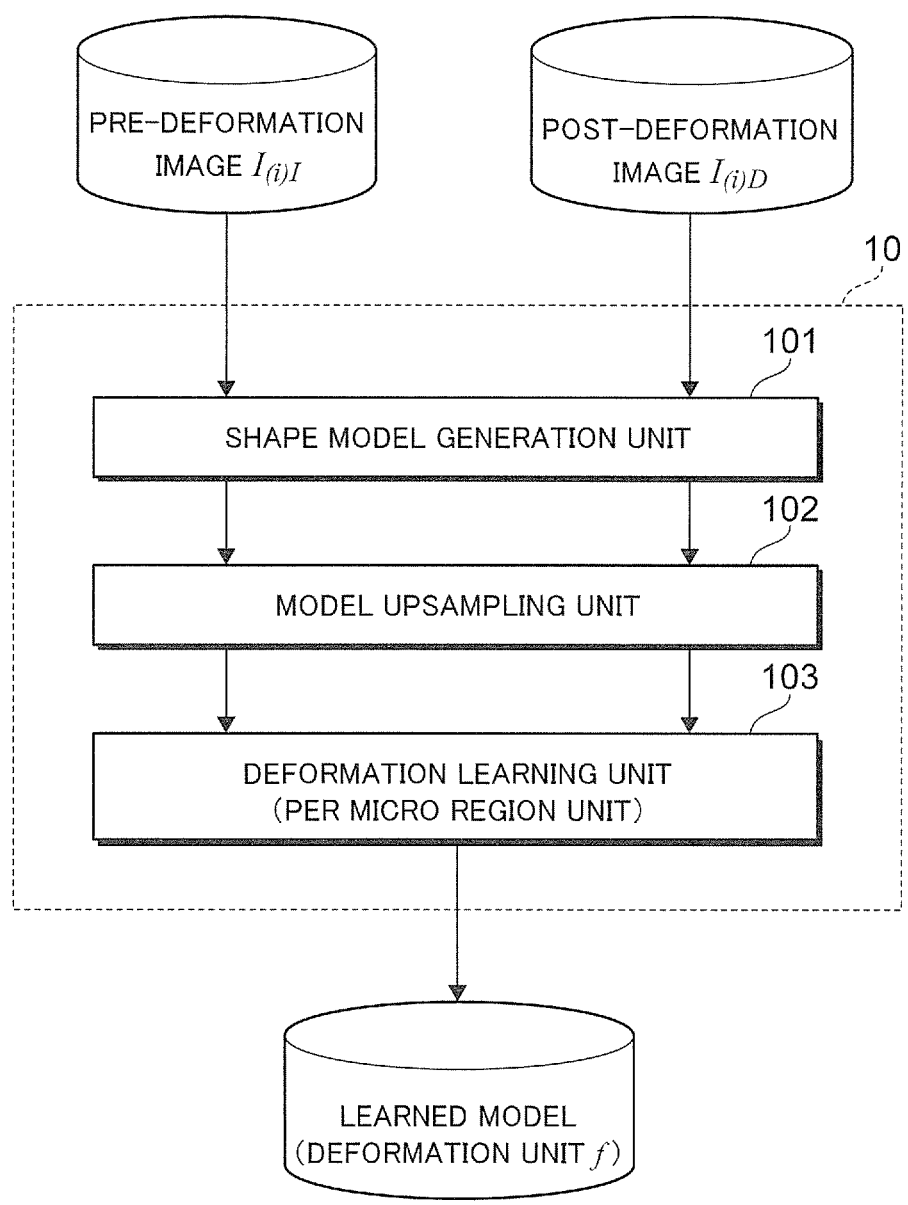
FIG. 3 shows an example of a functional configuration of the machine learning device.

FIG. 3 shows an example of a functional configuration of the machine learning device 10. The functional configuration shown in FIG. 3 is accomplished through execution of programs by the CPU 11 (refer to FIG. 2).

In FIG. 3, the image data acquired by capturing or measuring the object before deformation is shown as a pre-deformation image $I_{(i)I}$, and the image data similarly acquired by capturing or measuring the object after deformation is shown as a post-deformation image $I_{(i)D}$. The pre-deformation image $I_{(i)I}$ and the post-deformation image $I_{(i)D}$ are examples of measurement data before and after the deformation.

The machine learning device 10 in the exemplary embodiment functions as a shape model generation unit 101 generating vertex models from the pre-deformation image $I_{(i)I}$ and the post-deformation image $I_{(i)D}$, a model upsampling unit 102 generating multiple vertex models with different vertex dispositions from the generated vertex model, and a deformation learning unit 103 learning the relation between the feature amount of each micro region of the vertex model generated by upsampling and the displacement between the micro regions before and after the deformation.

All the vertex models in the exemplary embodiment are three-dimensional vertex models. Note that the three-dimensional vertex model may be defined by vertexes of a polygon mesh representing a surface by polygons, or by vertexes of a voxel mesh representing both a surface and an interior by voxels.

Unlike general learning, the learning here is performed, not on the entire vertex model, but per micro region unit constituting the vertex model. The deformation function f, which is the result of the learning, is output as a learned model.

There is no particular restriction on the object to be learned, but in the exemplary embodiment, the object is assumed to change the shape or position (or region) thereof. In the exemplary embodiment, the target of the learning is the lung, liver, stomach, bowel, kidney, pancreas and other organs of the specimen (for example, human or animal).

Figure 4A:
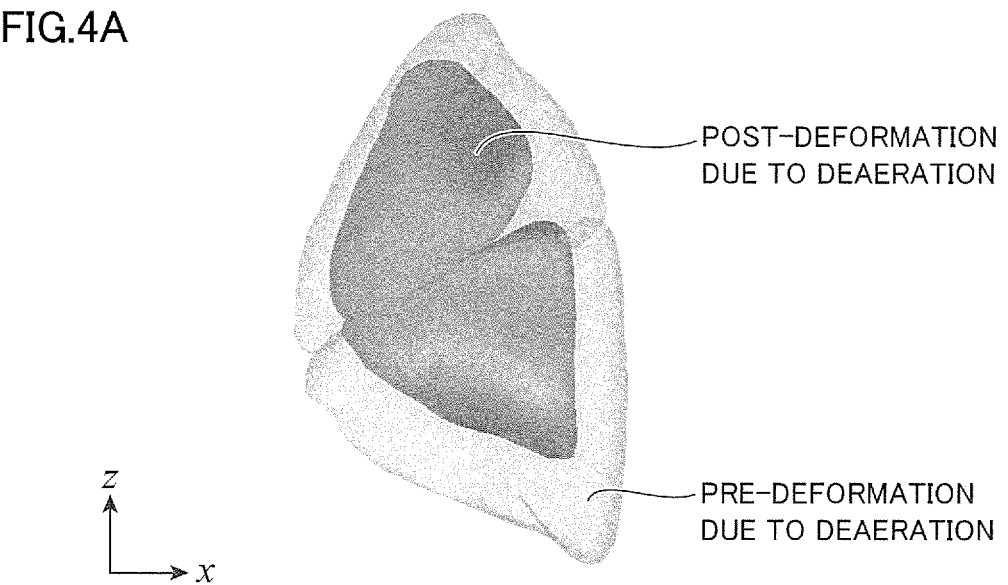
FIGS. 4A to 4C illustrate deformation of animal lungs due to deaeration, where
Figure 4B:
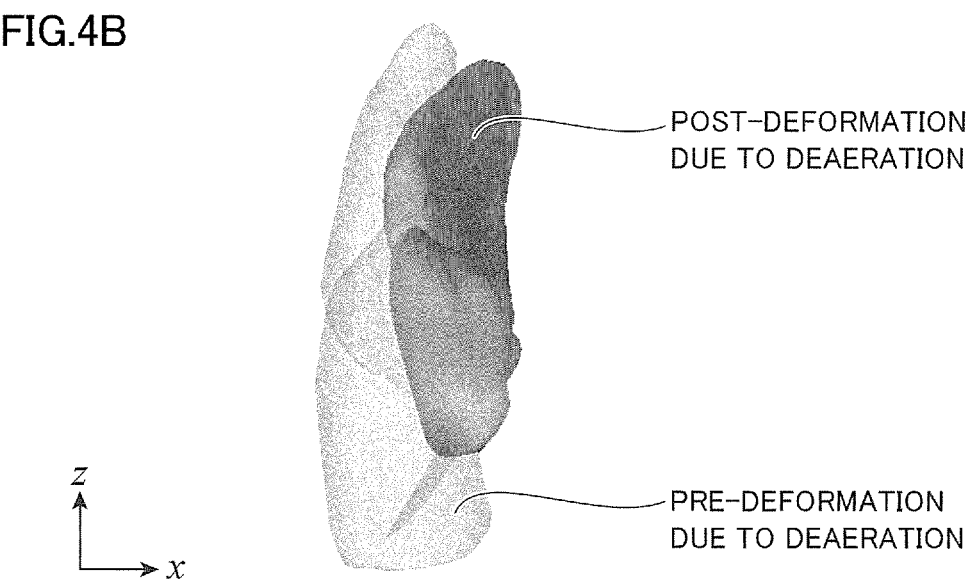
Figure 4C:
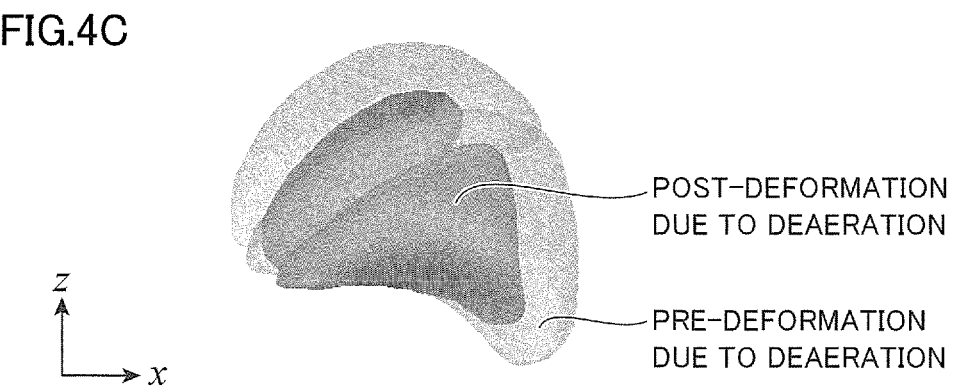

FIGS. 4A to 4C illustrate deformation of animal lungs due to deaeration. FIG. 4A shows a displacement model A, FIG. 4B shows a displacement model B, and FIG. 4C shows a displacement model C.

The laboratory beagle dog was used to generate the displacement models A, B and C. In the experiment, the bronchial pressure was changed from 14 cmH$_2$O to 2 cmH$_2$O, and the shape of the lung was measured with a three-dimensional CT.

In the exemplary embodiment, medical image data items captured the specimen's organs are used as the pre-deformation image $I_{(i)I}$ and the post-deformation image $I_{(i)D}$. Examples of the medical image data include the CT image data, the magnetic resonance imaging (MRI) image data, the X-ray image data, the ultrasonic wave image data, and the positron emission tomography (PET) image data. The medical image data may be the two-dimensional image data or the three-dimensional image data. The two-dimensional image data is represented by pixels defining the two-dimensional space, and the three-dimensional image data is represented by voxels (cubic unit cells), polygons, and the like defining the three-dimensional space. The medical image data is an example of the measurement data.

In the exemplary embodiment, the pre-deformation image $I_{(i)I}$ and the post-deformation image $I_{(i)D}$ are assumed to be the three-dimensional image. The three-dimensional image is defined, for example, by coordinates and voxel values. The voxel value differs depending on the image-capturing technique.

Let us return to the description of FIG. 3.

The shape model generation unit 101 generates the vertex models from the pre-deformation image $I_{(i)I}$ and the post-deformation image $I_{(i)D}$.

Figure 5:
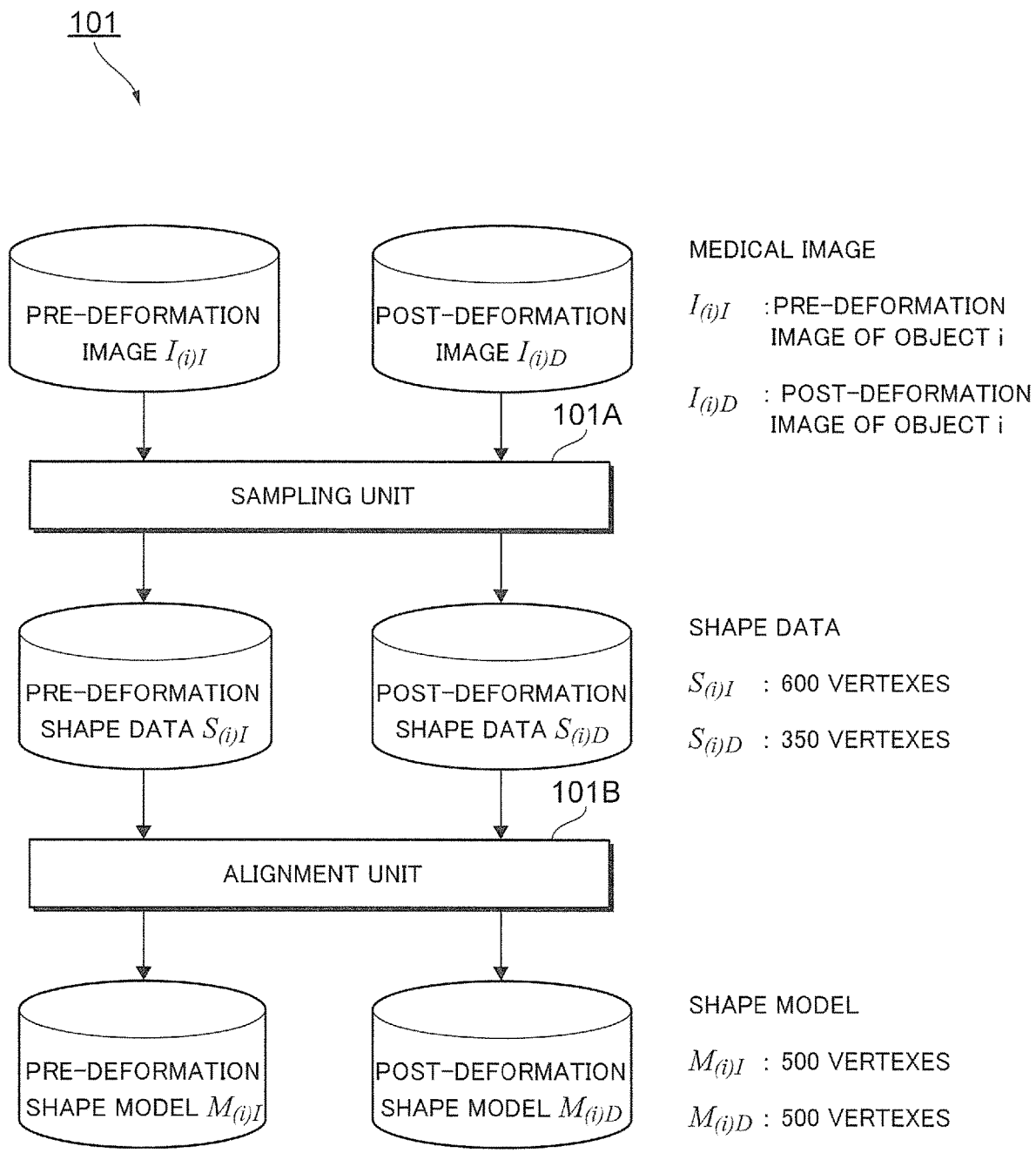
FIG. 5 illustrates an example of the processing executed in a shape model generation unit related to an exemplary embodiment.

FIG. 5 illustrates an example of the processing executed in the shape model generation unit 101 related to the exemplary embodiment.

The shape model generation unit 101 shown in FIG. 5 is configured with a sampling unit 101A and an alignment unit 101B.

The sampling unit 101A, for example, samples each of the pre-deformation image $I_{(i)I}$ and the post-deformation image $I_{(i)D}$ to generate shape data of the voxel mesh structure or the polygon mesh structure. Here, it is assumed that the shape data corresponding to the pre-deformation image $I_{(i)I}$ is $S_{(i)I}$ and the shape data corresponding to the post-deformation image $I_{(i)D}$ is $S_{(i)D}$.

The size of the pre-deformation image $I_{(i)I}$ and the post-deformation image $I_{(i)D}$ differs depending on the differences in the specimens and the image capturing conditions. In addition, there are limitations to unify the position and physical condition of the specimens during image capturing. For this reason, the number of vertexes of the voxels included in the independently-formed shape data $S_{(i)I}$ and $S_{(i)D}$ is inconsistent in general.

In the case of FIG. 5, the number of vertexes in the shape data $S_{(i)I}$ is 600, but the number of vertexes in the shape data $S_{(i)D}$ is 350.

Figure 6:
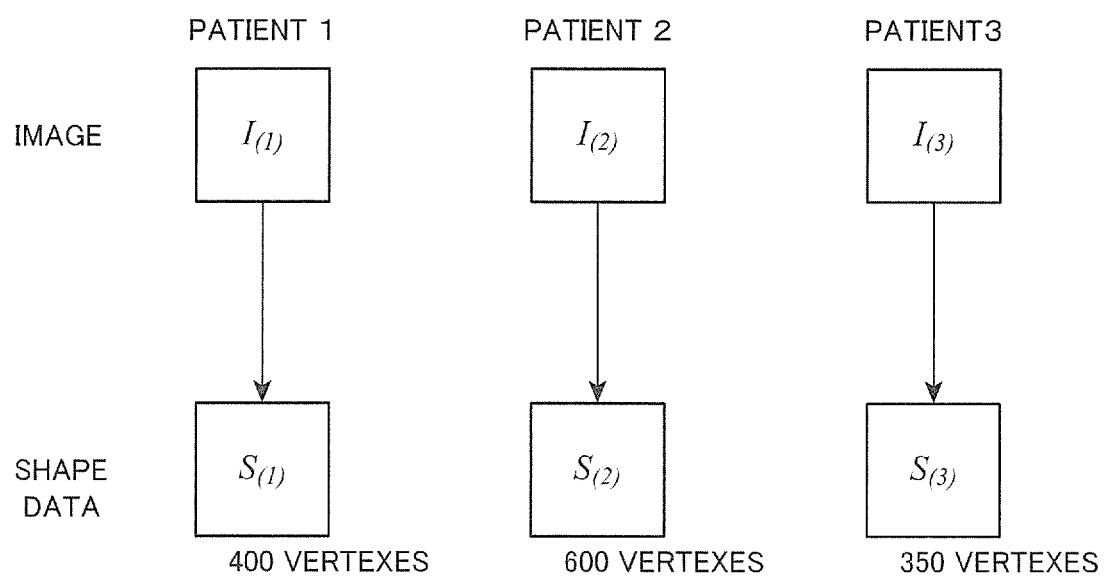
FIG. 6 illustrates differences in the number of vertexes due to different patients.

FIG. 6 illustrates differences in the number of vertexes due to different patients. In FIG. 6, while ignoring pre- or post-deformation, the image of the patient 1 is shown as $I_{(1)}$, the image 2 of the patient 2 is shown as $I_{(2)}$, the image 3 of the patient 3 is shown as $I_{(3)}$, and the corresponding shape data items are shown as $S_{(1)}$, $S_{(2)}$, and $S_{(3)}$, respectively.

In the case of FIG. 6, the number of vertexes in the shape data $S_{(1)}$ of the patient 1 is 400, the number of vertexes in the shape data $S_{(2)}$ of the patient 2 is 600, and the number of vertexes in the shape data $S_{(3)}$ of the patient 3 is 350.

Let us return to the description of FIG. 5.

When the shape data items $S_{(i)I}$ and $S_{(i)D}$ are obtained, the alignment unit 101B performs alignment between the shape data items. Specifically, the process of aligning the number of vertexes in each shape data is performed.

In FIG. 5, the shape data after the number of vertexes has been aligned is indicated as the shape model $M_{(i)}$. Hereinafter, the pre-deformation shape model is referred to as $M_{(i)I}$ and the post-deformation shape model is referred to as $M_{(i)D}$.

The pre-deformation shape model $M_{(i)I}$ is an example of the first shape model, and the post-deformation shape model $M_{(i)D}$ is an example of the second shape model.

In FIG. 5, the number of vertexes in the shape model $M_{(i)}$ is unified to 500.

Generation of the shape model $M_{(i)}$ with the unified number of vertexes enables statistical learning of deformation of the object.

Note that, in the case where the shape data items $S_{(i)I}$ and $S_{(i)D}$ are inputted to the shape model generation unit 101 (refer to FIG. 3) instead of the pre-deformation image $I_{(i)I}$ and the post-deformation image $I_{(i)D}$, processing in the sampling unit 101A can be omitted.

Figure 7:
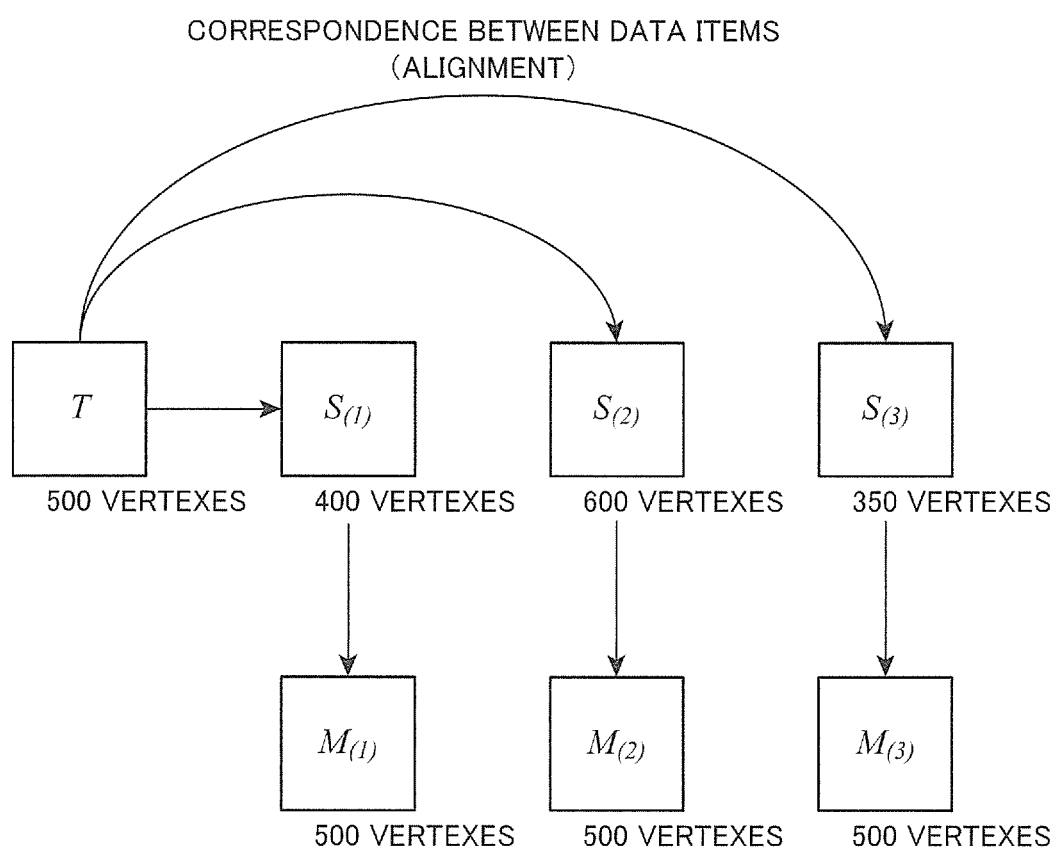
FIG. 7 illustrates aligning process executed by an alignment unit.

FIG. 7 illustrates the alignment process executed by the alignment unit 101B. As described above, the alignment process deforms a predefined template shape T to match the shape of the shape data $S_{(i)}$, to thereby generate the shape model $M_{(i)}$ with the number of vertexes unified to the number of vertexes of the template shape T, while having the same external shape as the shape data $S_{(i)}$. Here, the process of making the template shape T closer to the shape of the shape data $S_{(i)}$ is performed gradually from the whole to the parts.

The alignment by the alignment unit 101B (refer to FIG. 5) is also performed on the post-deformation shape data $S_{(i)D}$ subsequent to the pre-deformation shape data $S_{(i)I}$.

Figure 8:
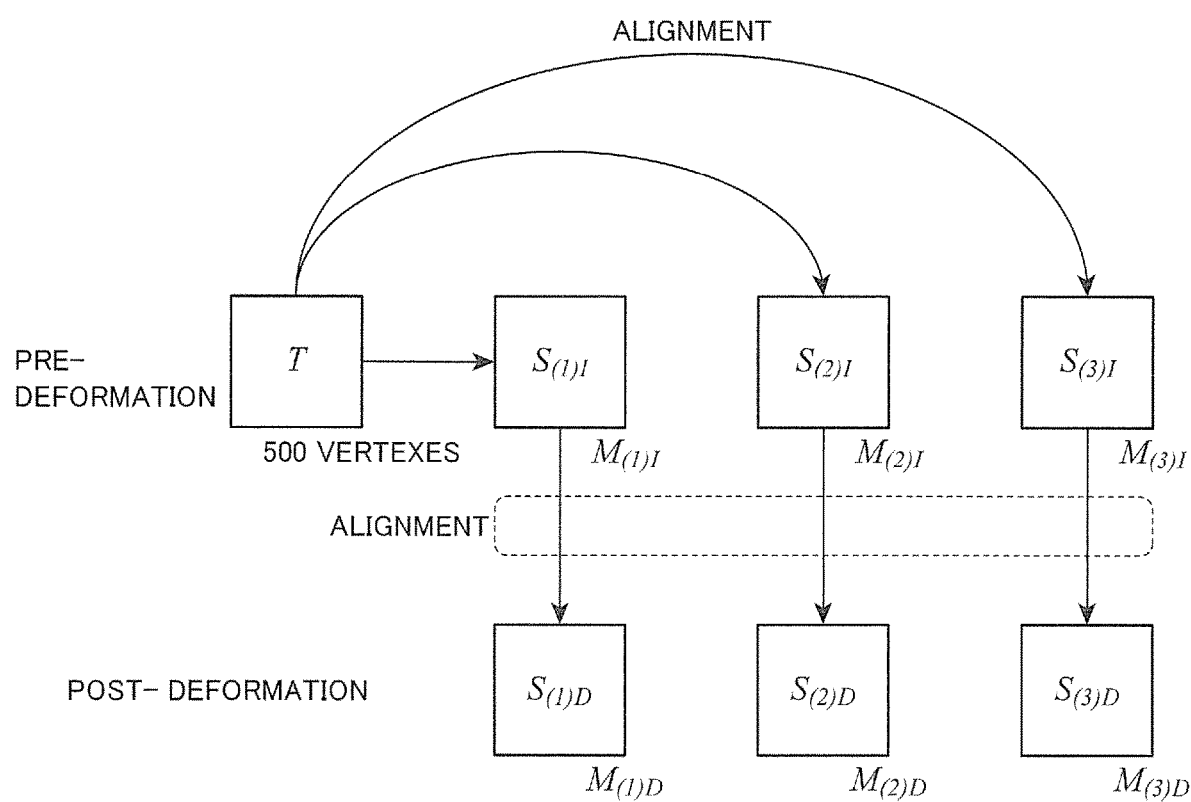
FIG. 8 illustrates an execution sequence of alignment of the shape data before deformation and alignment of the shape data after deformation.

FIG. 8 illustrates an execution sequence of alignment of the pre-deformation shape data $S_{(i)I}$ and alignment of the post-deformation shape data $S_{(i)D}$. First, by the alignment of the template shape T with the 500 vertexes, the shape models $M_{(1)I}$, $M_{(2)I}$, and $M_{(3)I}$ are generated from the pre-deformation data items $S_{(1)I}$, $S_{(2)I}$, and $S_{(3)I}$, respectively. Next, by aligning the pre-deformation shape model $M_{(i)I}$ having the 500 vertexes with the post-deformation shape data items $S_{(1)D}$, $S_{(2)D}$, and $S_{(3)D}$, the shape models $M_{(1)D}$, $M_{(2)D}$, and $M_{(3)D}$ are generated.

The two-stage alignment shown in FIG. 8 generates the shape models $M_{(i)I}$ and $M_{(i)D}$ by unifying the number of vertexes of the pre-deformation shape data $S_{(i)I}$ and the post-deformation shape data $S_{(i)D}$ to the number of vertexes of the template shape T.

Let us return to the description of FIG. 3.

The model upsampling unit 102 upsamples each of the shape models M(i)I and M(i)D generated by the shape model generation unit 101 to generate multiple shape models with similar shapes and structures but with different vertex locations.

However, the model upsampling section 102 is not indispensable in the case of dealing with objects that are easy to acquire images before and after deformation.

On the other hand, in the case of dealing with objects that are not easy to acquire images before and after transformation (for example, to deal with medical image data), it is possible to increase the number of teacher data items used for learning by providing the model upsampling unit 102. Even in the case of dealing with objects that are easy to acquire images, the number of the shape models $M_{(i)I}$ and $M_{(i)D}$ used for teacher data can be increased from fewer images by using the model upsampling unit 102.

Figure 9:
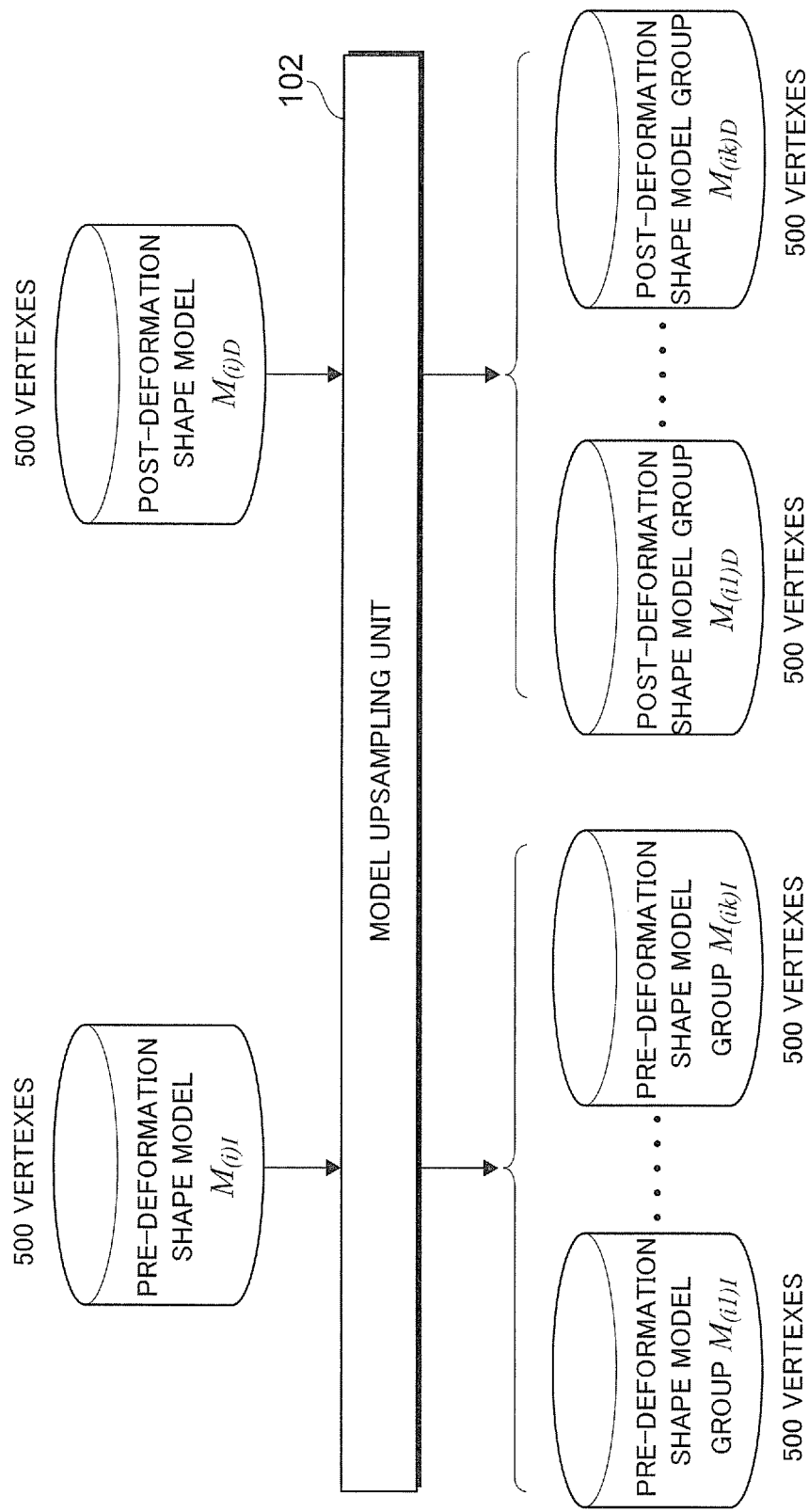
FIG. 9 illustrates upsampling operations by a model upsampling unit.

FIG. 9 illustrates upsampling operations by the model upsampling unit 102.

In the case of FIG. 9, the number of pre-deformation shape models $M_{(i)I}$ and the number of post-deformation shape models $M_{(i)D}$ are each increased k-fold. In other words, for one pre-deformation shape model $M_{(i)I}$, k shape models $M_{(i1)I}, \ldots, M_{(ik)I}$ are generated with different vertex locations, whereas, for one post-deformation shape model $M_{(i)D}$, k shape models $M_{(i1)D}, \ldots, M_{(ik)D}$ are generated with different vertex locations.

Here, the pre-deformation shape models $M_{(i1)I}, \ldots, M_{(ik)I}$ are an example of the third shape model, and the post-deformation shape models $M_{(i1)D}, \ldots, M_{(ik)D}$ are an example of the fourth shape model.

Of course, the generated shape models $M_{(i1)I}, \ldots, M_{(ik)I}$ and $M_{(i1)D}, \ldots, M_{(ik)D}$ are all composed of 500 vertexes.

In this way, upsampling generates the shape models with different vertex locations because, in the exemplary embodiment, the displacements are learned in the small region units of the shape model (for example, vertex units).

As described above, the upsampling operations by the model upsampling unit 102 can be omitted in the case where a sufficient number of measurement data items are available in advance.

Figure 10:
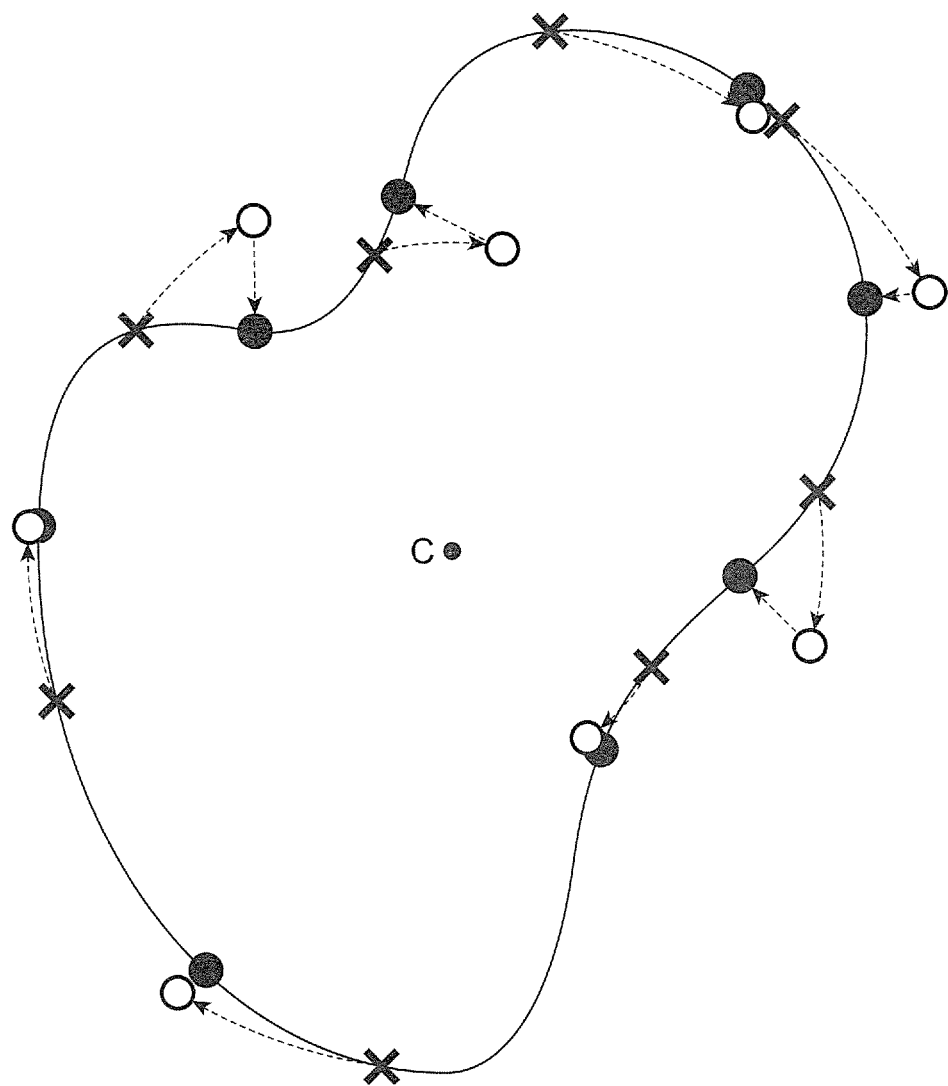
FIG. 10 illustrates an example of the upsampling methods in the exemplary embodiment.

FIG. 10 illustrates an example of the upsampling methods in the exemplary embodiment.

FIG. 10 shows only the vertexes positioned on the surface among each of the 500 vertexes (indicated by the crosses in the figure) composing the shape models $M_{(i)I}$ and $M_{(i)D}$, due to construction constraints and for convenience of explanation.

The method shown in FIG. 10 is to rotate the 500 vertexes of the shape model in a direction centered at a point determined in the shape model (the center of gravity C, for example), and thereafter, linearly move the vertexes (shown as white circles in the figure) that were located on the surface to the nearest position of the surface before rotation (shown as the curve in the figure).

As a result, each vertex (indicated by a cross in the figure) that was on the surface before rotation is moved to the position indicated by a black circle. In the rotation and linear movement, each vertex in the shape model is repositioned so that relative positional relationship with the vertex on the surface is preserved. For example, in the case where the entire shape model is represented with tetrahedral elements, it is possible to parameterize the relative position of the interior of the tetrahedron.

Note that, if the center of rotation is changed, different upsampling models can be generated even if the same processing process is performed. Similarly, the different upsampling models can be generated by changing the direction of rotation. The different upsampling models can also be generated by changes in the rules during linear movement.

The upsampling shown in FIG. 10 is capable of generating multiple shape models with different vertex locations, while maintaining the external shape and the number of vertexes of the shape models.

Figure 11:
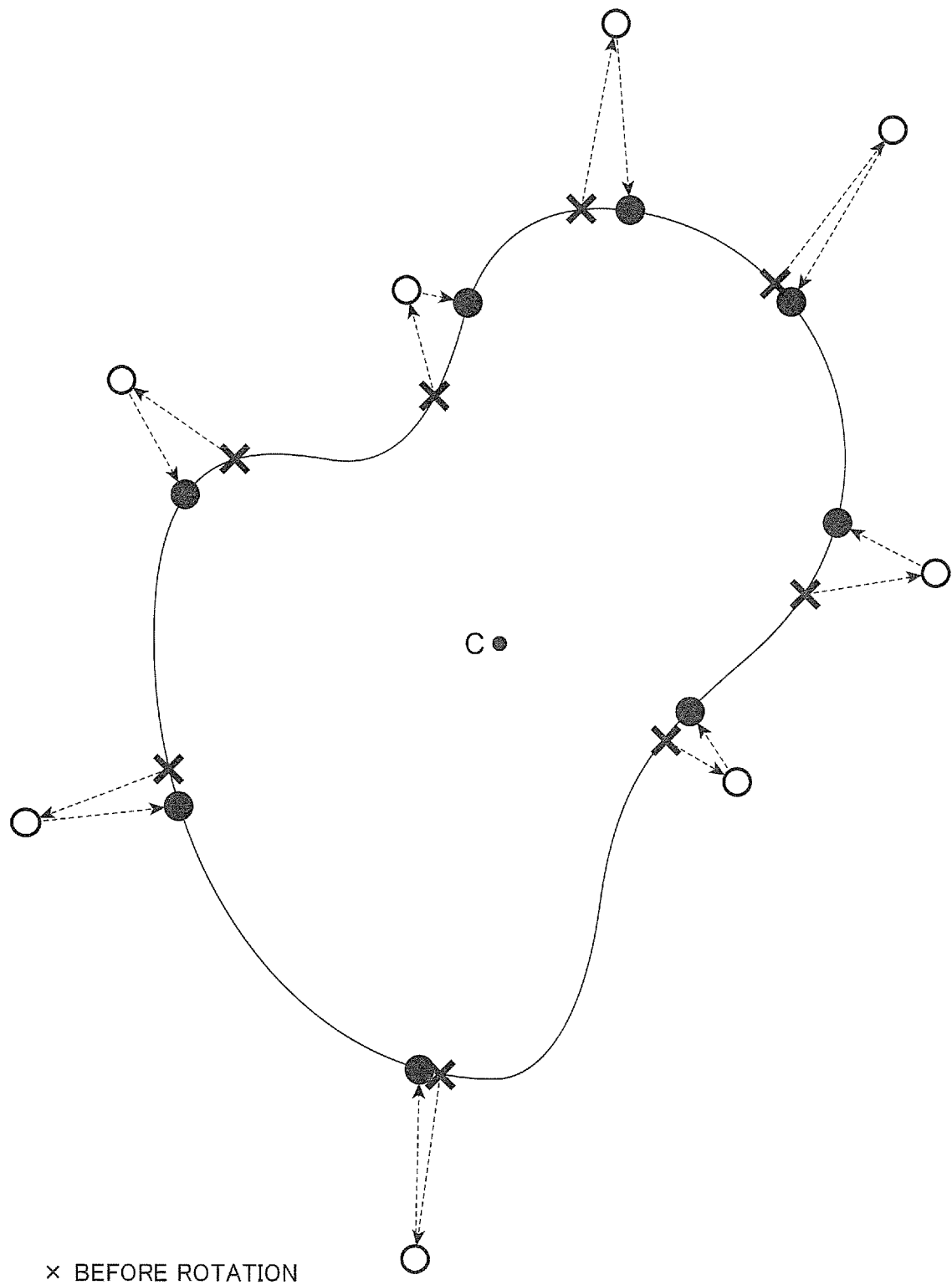
FIG. 11 illustrates another example of the upsampling methods in the exemplary embodiment.

FIG. 11 illustrates another example of the upsampling methods in the exemplary embodiment.

FIG. 11 also shows only the vertexes positioned on the surface among each of the 500 vertexes (indicated by the crosses in the figure) composing the shape models $M_{(i)I}$ and $M_{(i)D}$, due to construction constraints and for convenience of explanation.

The method shown in FIG. 11 is to perform enlarging conversion (outward movement) of the 500 vertexes of the shape model centered at a point determined in the shape model (the center of gravity C, for example), and thereafter, linearly move the vertexes (shown as white circles in the figure) that were located on the surface to the nearest position of the surface before enlarging conversion (shown as the curve in the figure).

As a result, each vertex (indicated by a cross in the figure) that was on the surface before enlarging conversion is moved to the position indicated by a black circle. In the enlarging conversion and linear movement, each vertex in the shape model is repositioned so that relative positional relationship with the vertex on the surface is preserved.

Note that, if the position of the center used for enlarging conversion is changed, different upsampling models can be generated even if the same processing process is performed. Similarly, the different upsampling models can be generated by changing the enlargement factor. The different upsampling models can also be generated by changes in the rules during linear movement.

The upsampling shown in FIG. 11 is capable of generating multiple shape models with different vertex locations, while maintaining the external shape and the number of vertexes of the shape models.

Note that, as the method of perturbation (reposition) of the vertex position by upsampling, the method of repositioning each vertex to approximately match the original shape after the reducing conversion, or randomly perturbating the vertex position may be used.

Moreover, in the above description, the vertexes on the surface among the rotated vertexes are aligned to move linearly to the surface of the original shape model; however, the alignment by linear movement may be performed under a weak constraint. The weak constraint means that errors within a predetermined range are allowed.

The upsampling operation by the model upsampling unit 102 can generate multiple shape models with similarly represented shapes and structures but with different vertex locations. In other words, teacher data can be increased.

Let us return to the description of FIG. 3.

The deformation learning unit 103 learns the relation between the pre-deformation shape models $M_{(i1)I}$ to $M_{(ik)I}$ generated by the above-described process and the post-deformation shape models $M_{(i1)D}$ to $M_{(ik)D}$.

In the case of the exemplary embodiment, the deformation is learned per micro region (for example, vertex) unit.

Figure 12:
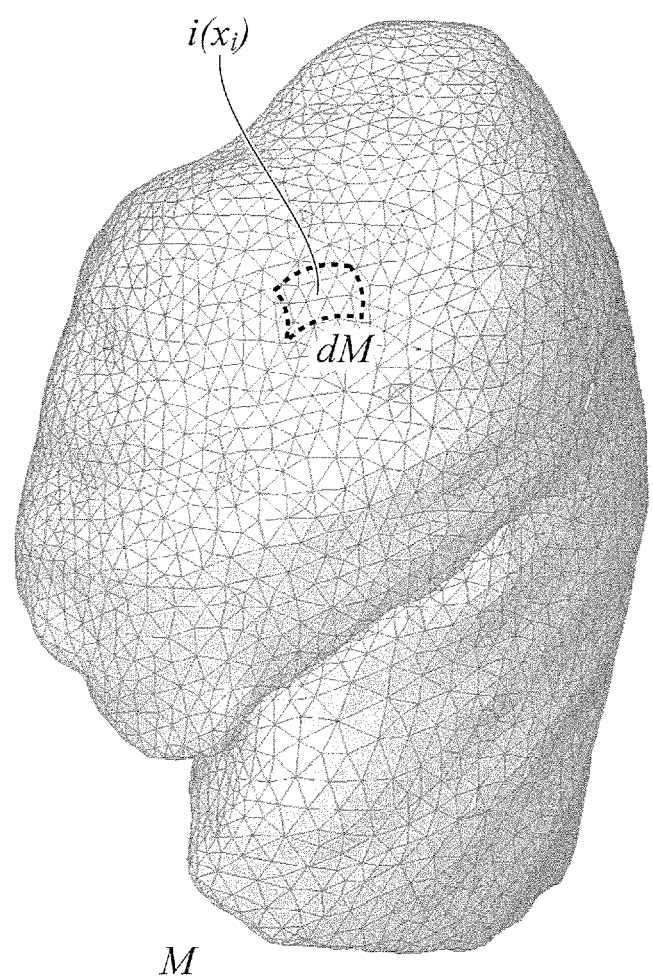
FIG. 12 illustrates a relation between the shape model of the lungs and the micro region.
Figure 13:
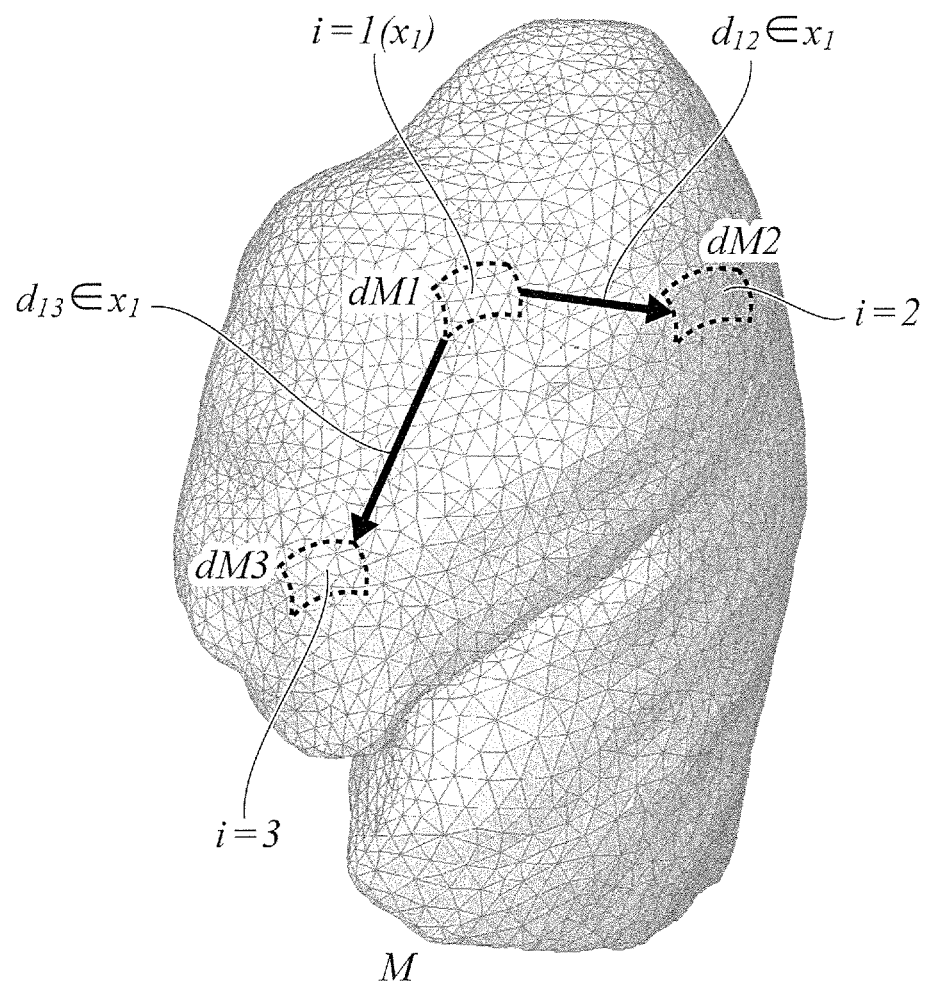
FIG. 13 illustrates an input/output relation to be learned in an exemplary embodiment.
Figure 13:
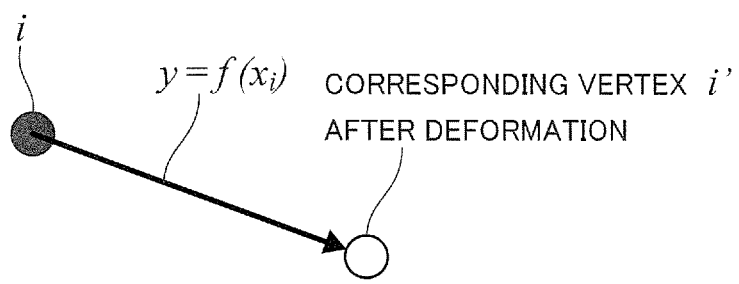

FIGS. 12 and 13 show the concept of learning in the exemplary embodiment.

FIG. 12 illustrates a relation between a shape model M of a lung and a micro region dM. By learning per micro region unit, learning data items of the number of micro regions that can be acquired from a single measurement data item. In the case of the exemplary embodiment, use of a vertex as a micro region means that 500 learning data items can be generated from a single measurement data item. Of course, learning data items generated by the number of measured data items are doubled.

FIG. 13 illustrates an input/output relation to be learned in the exemplary embodiment.

In the exemplary embodiment, the feature amount data $x_i$ regarding each vertex i of the pre-deformation shape model is used as the input, and the displacement amount data $y_i$ regarding the corresponding vertex i before and after deformation is used as the output. At the learning stage, both the feature amount data $x_i$ and the displacement amount data $y_i$ are given, and the deformation function f defining the relation between the two values is learned.

In the exemplary embodiment, the difference between micro regions on the same shape model (for example, the difference between vertexes d) is used as the feature amount data $x_i$.

FIG. 13 shows a vertex 1 and other vertexes 2 and 3 and the differences $d_{12}$ and $d_{13}$ as a specific example of the difference between vertexes d, which is an example of the feature amount data $x_i$.

In actuality, the difference d is calculated between one vertex i and 500 vertexes (micro regions). Here, when the coordinates of each vertex are expressed by $v_i$ and $v_j$, the difference between vertexes $d_{ij}$ with respect to vertex i is expressed as $d_{ij}$=(where j=1, 2, 3, ..., 500).

Consequently, the feature amount data $x_i$ with respect to the vertex i is defined as a set of 500 differences between vertexes $d_{ij}$. As will be described later, the difference between vertexes $d_{ij}$ is an example of the feature amount data $x_i$.

In FIG. 13, all the vertexes 1, 2, and 3 are drawn discretely, but this is only for the description of the difference between vertexes $d_{ij}$, and the actual positions are not limited to the example shown in FIG. 13.

Figure 14:
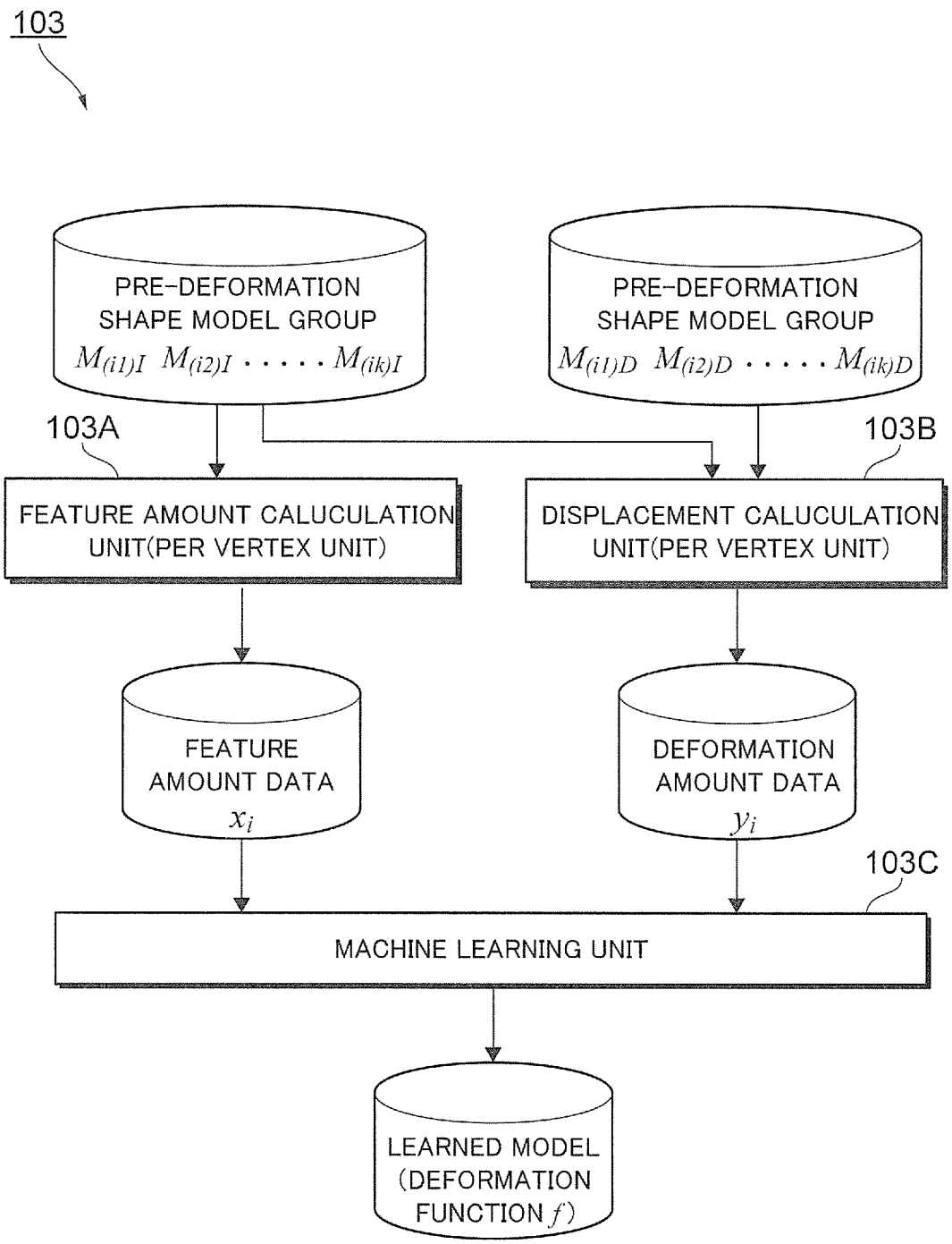
FIG. 14 illustrates an example of the processing executed in a deformation learning unit related to an exemplary embodiment.

FIG. 14 illustrates an example of the processing executed in the deformation learning unit 103 related to the exemplary embodiment.

The deformation learning unit 103 shown in FIG. 14 is configured with: a feature amount calculation unit 103A calculating the feature amount data $x_i$ for each vertex of the individual shape model that is the element of the pre-deformation model group; a displacement calculation unit 103B calculating the displacement amount data $y_i$ between the corresponding vertexes i of the shape model before and after the deformation; and the machine learning unit 103C learning the relation between the calculated feature amount data $x_i$ and the displacement amount data $y_i$.

The feature amount calculation unit 103A in the exemplary embodiment calculates the feature amount data $x_i$ per each vertex of the shape models $M_{(i1)I}$ to $M_{(ik)I}$ generated from the measurement data before deformation given for learning.

As described above, in the case of the exemplary embodiment, the feature amount data $x_i$ is given as the difference between vertexes $d_{ij}$ for all vertexes constituting the shape model $M_{(i)I}$ generated from the measurement data before deformation inputted for learning. In other words, 500 feature amount data items $x_i$ are calculated for a single shape model $M_{(i)I}$.

In the case of FIG. 14, the number of elements in the pre-deformation model group is k, and accordingly, 500×k feature amount data items $x_i$ are calculated. In actuality, the feature amount data items $x_i$ of the number multiplied by the number of inputted measurement data items A are calculated.

The displacement calculation unit 103B in the exemplary embodiment calculates the displacement amount data $y_i$ between the corresponding vertexes of the shape models in the relation of before and after the deformation. For a single shape model before and after deformation, 500 displacement amount data items $y_i$ are calculated.

The machine learning unit 103C in the exemplary embodiment learns the deformation function f(i) expressing the relation between the feature amount data $x_i$ for each vertex i of the pre-deformation shape model M(j)I and the displacement amount data $y_i$ between the shape models before and after deformation for the same vertex i.

Figure 15:
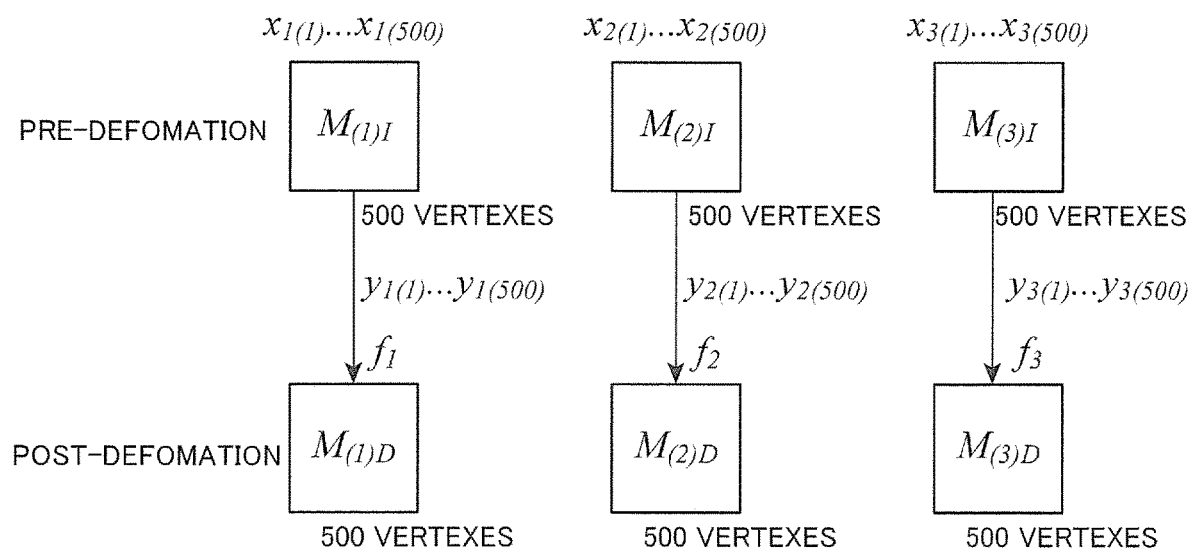
FIG. 15 illustrates a relation learned in a machine learning unit to be related to an exemplary embodiment.

FIG. 15 illustrates the relation learned in the machine learning unit 103C related to the exemplary embodiment.

In FIG. 15, the deformation function that learned the relation between the feature amount data items $x_{1(1)}, \ldots, x_{1(500)}$ for each vertex i of the pre-deformation shape model $M_{(1)I}$ (I=1, ..., 500) and the displacement amount data $y_{1(1)}, \ldots, y_{1(500)}$ between the corresponding vertexes is expressed by $f_1$. The same is true for the shape models $M_{(2)I}$ and $M_{(3)I}$.

In the exemplary embodiment, the kernel regression model represented by expression 1 is used as a regression model representing the deformation function f.

[Expression 1]

$$y_i = \sum_{i=0}^{n} \alpha_i k(x_i, x) \quad \text{(Expression 1)}$$

Here, $k(x_i, x)$ is the kernel function given by the following expression.

$$K(x_i, x) = \exp(-\beta \|x_i - x\|^2)$$

Note that $\|x_i - x\|^2$ is the $L^2$ norm corresponding to the difference between vertexes $d_{ij}$ between the vertex i and the other vertex j on the same shape model. In other words, $k(x_i, x)$ corresponds to the feature amount data $x_i$ for the vertex i. The individual $a_i k(x_i, x)$ corresponds to $f_i$ (i=1, 2, 3) in FIG. 15.

The displacement calculation unit 103B in the exemplary embodiment learns the coefficient $a_i$ for each vertex i. The coefficient $a_i$ is an update parameter.

The set of learned coefficients $a_i$ may be provided to the deformation estimation device 20 (refer to FIG. 1) as the learned model, or the newly learned coefficients $a_i$ may be transmitted to the deformation estimation device 20 to update the learned model.

<Specific Examples of Learned Models>

For example, medical image data of human lungs can be obtained as pre-surgical and post-surgical CT data of a patient with pneumothorax.

The pre-surgical CT data is CT data of collapsed lung and the post-surgical CT data is CT data of normal lung (after treatment).

In this case, the post-surgical CT data is used as the pre-deformation medical image data and the pre-surgical CT data is used as the post-deformation medical image data to learn the relation before and after the deformation as the learned model. The learned model can be used to predict lung deformation during surgery in the case where a patient with ordinary lung has surgery.

<Deformation Estimation Device>

Figure 16:
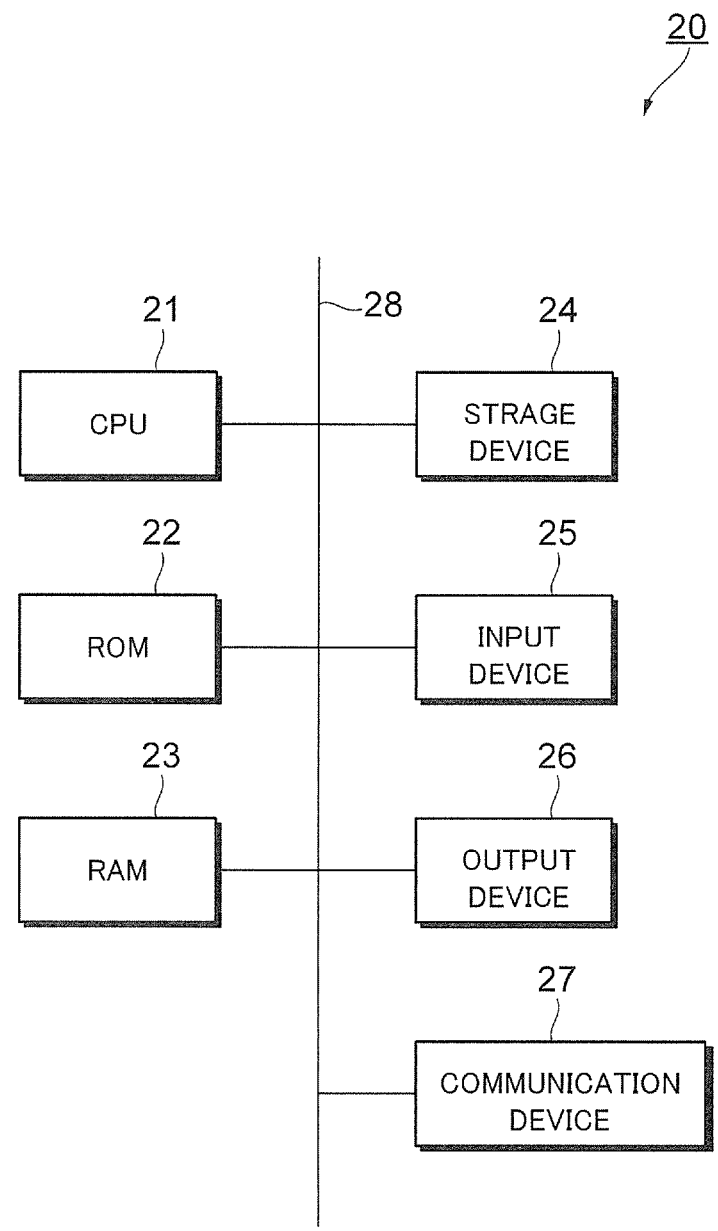
FIG. 16 shows an example of a hardware configuration of a deformation estimation device.

FIG. 16 shows an example of a hardware configuration of the deformation estimation device 20 (refer to FIG. 1).

The deformation estimation device 20 shown in FIG. 16 includes: a central processing unit (CPU) 21 controlling the entire device through execution of programs (including basic software); a ROM 22 storing programs, such as the basic input output system (BIOS); and a random access memory (RAM) 23 used as execution regions of the programs. The CPU 21, the ROM 22, and the RAM 23 in this case constitute a so-called computer and execute various kinds of information processing. Note that the ROM 22 is configured with a nonvolatile semiconductor memory.

A storage device 24, for example, is configured with a hard disk device, and stores application programs estimating the deformed shape of any measurement data given by the terminal 50 (refer to FIG. 1) using the learned model learned by the machine learning device 10 and estimation results. Note that the storage device 24 is not limited to the internal device, but may be an external device, or a networked storage.

An input device 25, for example, is a keyboard or a mouse, and is used for operation inputting. An output device 26 is a display device or a printing device used to display operation screens or to print information. Note that, in the case where the deformation estimation device 20 is implemented as a server, the input device 25 and the output device 26 may be provided on the not-shown terminal side.

A communication device 27 is used to communicate with external devices. The communication device 27 is used to input the measurement data from the terminal 50 and to output the estimation results to the terminal 50.

The CPU 21 and each component are connected via a bus 28 and not-shown signal wires.

Note that the deformation estimation device 20 can also be implemented as dedicated hardware.

Figure 17:
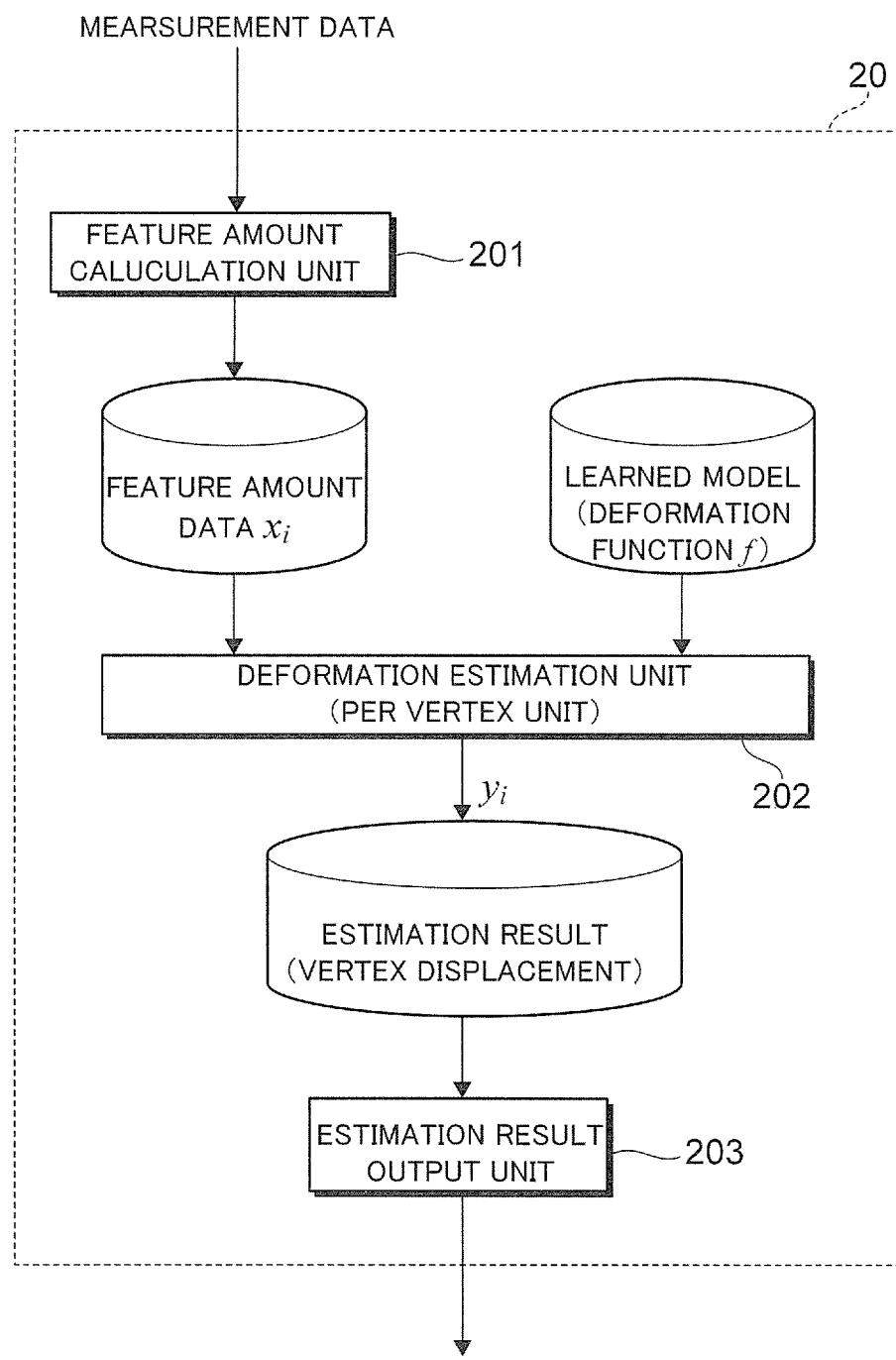
FIG. 17 shows an example of a functional configuration of the deformation estimation device.

FIG. 17 shows an example of a functional configuration of the deformation estimation device 20. The functional configuration shown in FIG. 17 is accomplished through execution of programs by the CPU 21 (refer to FIG. 16).

The deformation estimation device 20 in FIG. 17 functions as: a feature amount calculation unit 201 calculating the feature amount data $x_i$ for each vertex i from the pre-deformation measurement data inputted through the terminal 50; a deformation estimation unit 202 estimating the displacement amount data $y_i$ of the vertex i by applying the calculated feature amount data $x_i$ to the learned model; and an estimation result output unit 203 estimating the shape after deformation from the displacement amount data $y_i$ of all the vertexes i and outputting the estimated shape.

Figure 18:
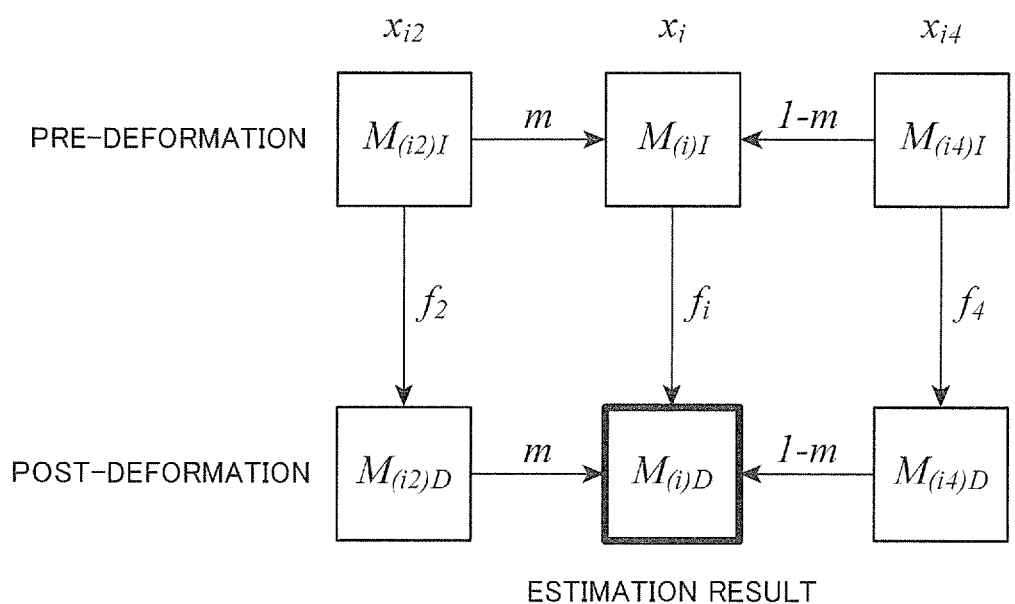
FIG. 18 shows an estimation process by the deformation estimation device.

FIG. 18 illustrates an estimation process by the deformation estimation device 20.

When any measurement data $M_{(i)I}$ is given from terminal 50 (refer to FIG. 1), the feature amount calculation unit 201 (refer to FIG. 17) calculates the feature amount data $x_i$ for each vertex i. Next, the deformation estimation unit 202 (refer to FIG. 17) extracts the shape models $M_{(i2)I}$ and $M_{(i4)I}$ having feature data items $x_{i2}$ and $x_{i4}$ similar to the feature amount data $x_i$ to be processed.

In FIG. 18, the similarity of the feature amount data $x_i$ is determined with the internal ratio m:1−m. Here, m is a real number not less than 0 and not more than 1.

Further, the deformation estimation unit 202 generates the deformation function $f_i$ acquired by linearly interpolating the learned models (namely, the deformation functions $f_2$ and $f_4$) regarding the multiple extracted shape models $M_{(i2)I}$ and $M_{(i4)I}$, and estimates the displacement amount data $y_i$ corresponding to the feature amount data $x_i$ by using the generated deformation function $f_i$.

In the exemplary embodiment, the deformation function $f_i$ is generated by use of linear interpolation, but nonlinear interpolation can be used to generate the deformation function $f_i$.

Figure 19:
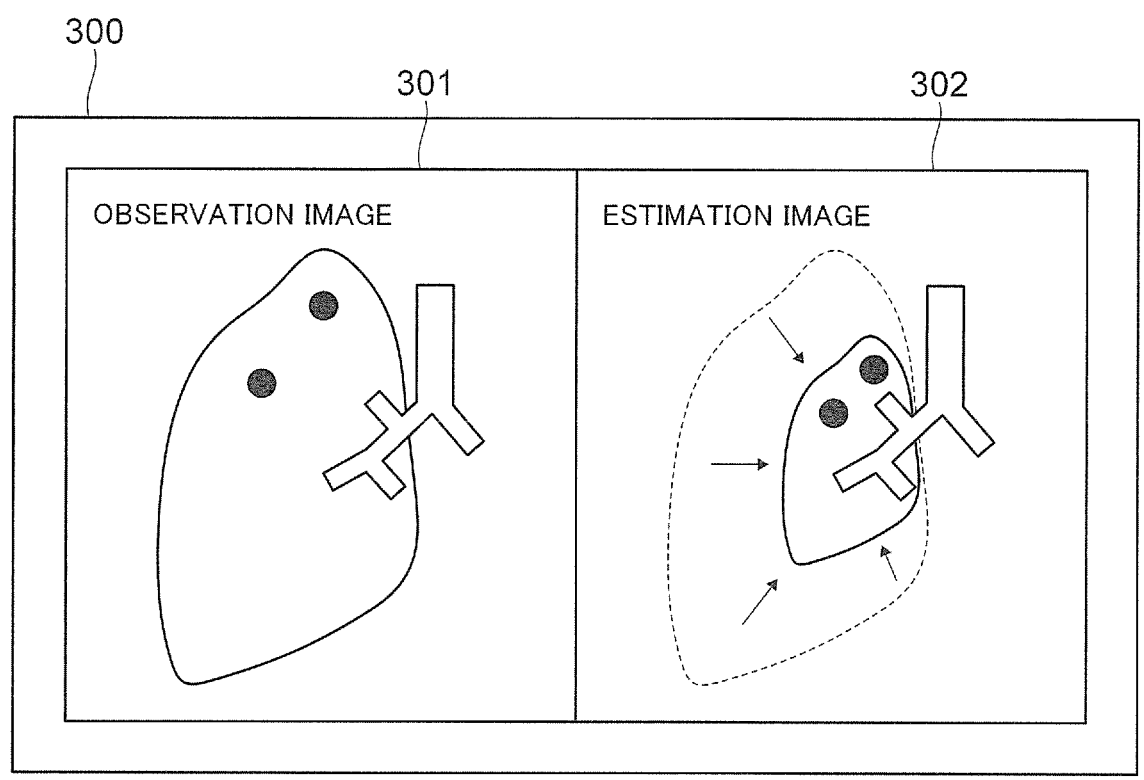
FIG. 19 illustrates an example of an output screen by an estimation result output unit.

FIG. 19 illustrates an example of an output screen 300 by the estimation result output unit 203 (refer to FIG. 17).

The output screen 300 has a pre-deformation observation image section 301 disposed on the left and an estimation image section 302 corresponding to the post-deformation shape disposed on the right.

In the case of FIG. 19, there are two nodules inside the lung. The lung image displayed in in the observation image section 301 is a pre-surgical image. The lung is inflated.

The lung shown in the estimation image section 302 is an estimated image during surgery. The lung during surgery is deflated by deaerated deformation. As shown in FIG. 19, it is possible to estimate the location of the nodules as well as the external shape.

<Estimation Error>

Hereinafter, description will be given of the error between the estimation results by the above technique and the actually measured values.

Experimental Conditions

Measurement of living lung data of 11 beagle dogs

Modeling of the superior lobe with 204 vertexes and the inferior lobe with 200 vertexes Upsampling of the living lung data measured at the aerated condition by enlarging and reducing the data to ±2.5 mm, ±5.0 mm, ±7.5 mm Use of 80% of the measurement data for training data and 20% for test data Evaluation Comparison of the following regression models using the Hausdorff distance as the error index Regression models (multiple linear regression models, Lasso regression models, kernel regression models)

Feature amount data (4 types)

The Hausdorff distance is the distance given as the maximum value of deviation between two shapes.

FIG. 20 explains differences in estimation errors among the three types of regression models.

The values shown in FIG. 20 were used to try the regularization parameters of each regression model in about 10 ways, and the one with the smallest error was selected.

In the case of FIG. 20, the kernel regression model has the smallest estimation error. Incidentally, the estimation error of the superior lobe was 3.1±0.9 mm, and the estimation error of the inferior lobe was 3.9±1.9 mm.

The kernel regression model used in the exemplary embodiment was approximately one-third of the multiple linear regression model or the Lasso regression model (L1 regularization).

FIG. 21 explains differences in estimation errors among the four types of feature amount data.

The four types of feature amount data are assumed to be the following feature amount groups 1 to 4 regarding the vertex i.

Feature amount group 1: Coordinates $v_i$, normal vector $n_i$, curvature (second derivative, discrete Laplacian) $l_i$, difference between vertexes $d_{ij}$, shrinkage ratio $s_i$, Voronoi area $r_i$ Feature amount group 2: Difference between vertexes $d_{ij}$ Feature amount group 3: Difference between vertexes $d_{ij}$, normal vector $n_i \times 100$ Feature amount group 4: Coordinates $v_i$, normal vector $n_i$, curvature (second derivative, discrete Laplacian) $l_i$, shrinkage ratio $s_i$, Voronoi area $r_i$ The feature amount group 2 corresponds to the feature amount data $x_i$ used in the previous description.

From the diagram shown in FIG. 21, it is understood that only feature amount group 4, which does not include the difference between vertexes $d_{ij}$, has a large estimation error.

From the above, it is found that inclusion of the difference between vertexes $d_{ij}$ in the feature amount data is useful for increasing the estimation accuracy.

FIG. 22 shows the error between the estimation result and the actually measured value for each specimen in the case of using the kernel regression model as the regression model with feature amount data including the difference between vertexes $d_{ij}$.

Figure 23:
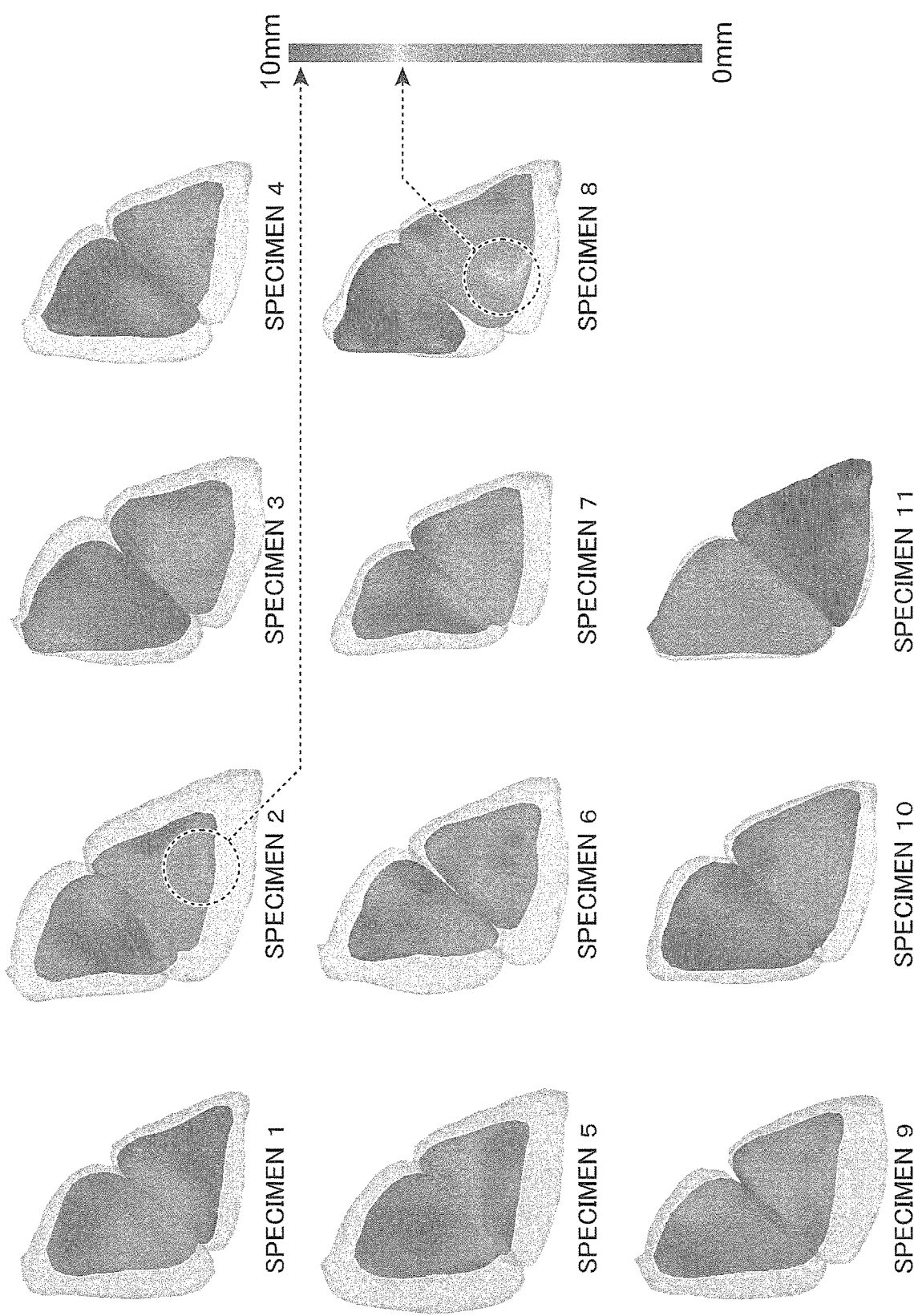
FIG. 23 shows a two-dimensional relation between the shapes of each specimen before and after deformation.

FIG. 23 shows a two-dimensional relation between the shapes of each specimen before and after deformation.

The specimens in FIG. 22 are the same as those in FIG. 23.

Only the specimen 2 has the estimation error of more than 5 mm in the superior lobe, and the specimens 2 and 8 have the estimation error of more than 5 mm in the inferior lobe.

In this experiment, the estimation error is relatively large in the lung with a much larger inferior lobe than the superior lobe, but in the lung with the superior lobe smaller than the inferior lobe and the superior lobe approximately the same size as the inferior lobe, the estimation error is small.

Note that, for the models estimated by the statistical mean displacement for the entire shape, errors of 10 mm or more were found; accordingly, reduction in the estimation error can be found in the technique of the exemplary embodiment.

Figure 24:
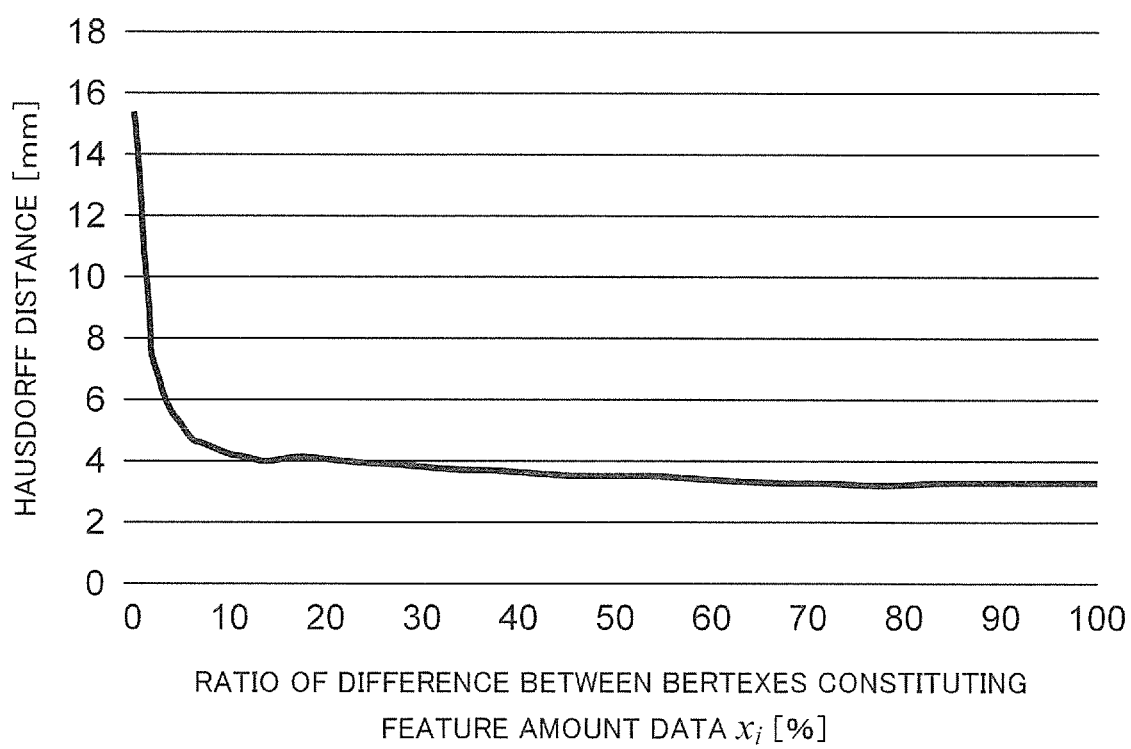
FIG. 24 illustrates a relation between the dimension of the differences among vertexes and the estimation accuracy.

FIG. 24 shows a relation between the dimension of the difference between vertexes and the estimation accuracy.

FIG. 24 shows the results of the experiment on the superior lobes. In the case of FIG. 24, the horizontal axis is the ratio of the difference between vertexes constituting the feature amount data $x_i$ for the vertex i, and the vertical axis is the Hausdorff distance indicating the estimation accuracy.

The ratio of the horizontal axis represents the case in which all the vertexes constituting the shape model $M_{(i)I}$ are used to calculate the difference between vertexes $d_{ij}$ as 100%. Consequently, in the case where the number of vertexes is 500, the ratio of the difference between vertexes constituting the feature amount data $x_i$ being 10% means that the feature amount data $x_i$ for the vertex i is given by the 50 differences between vertexes $d_{ij}$. The vertical axis is in the unit of mm.

In the above description, the example in which the feature quantity data $x_i$ is given as the difference between vertexes $d_{ij}$ by the number of vertexes was explained; however, it was found that the estimation accuracy of 5 mm or less was obtained by defining the feature amount data $x_i$ by a difference between vertexes $d_{ij}$ of approximately 5% or more. It is preferable to define the feature amount data $x_i$ with the difference between vertexes $d_{ij}$ of approximately 10% or more, and it is more preferable to define the feature amount data $x_i$ with the difference between vertexes $d_{ij}$ of approximately 15% or more for obtaining stable estimation accuracy.

Application Example

By integrating the above-described estimation system 1 (refer to FIG. 1) or the deformation estimation device 20 (refer to FIG. 1) estimating deformation of target organs by use of the learned model generated by the machine learning device 10 into the surgery support system, or by coordinating the estimation system 1 or the deformation estimation device 20 with the surgery support system, displacement of a tumor in a new patient can be identified before surgery.

For example, the output screen 300 shown in FIG. 19 may be used as a screen example for use in the surgery support system. In this case, the terminal 50 (refer to FIG. 1) is used as the operating terminal for the surgery support system.

Exemplary Embodiment 2

Exemplary embodiment 1 described estimation of deformation of a single organ from the pre-deformation medical image data; however, here, description will be given of a case in which deformation or movement in the positions of multiple organs is to be estimated.

Figure 25:
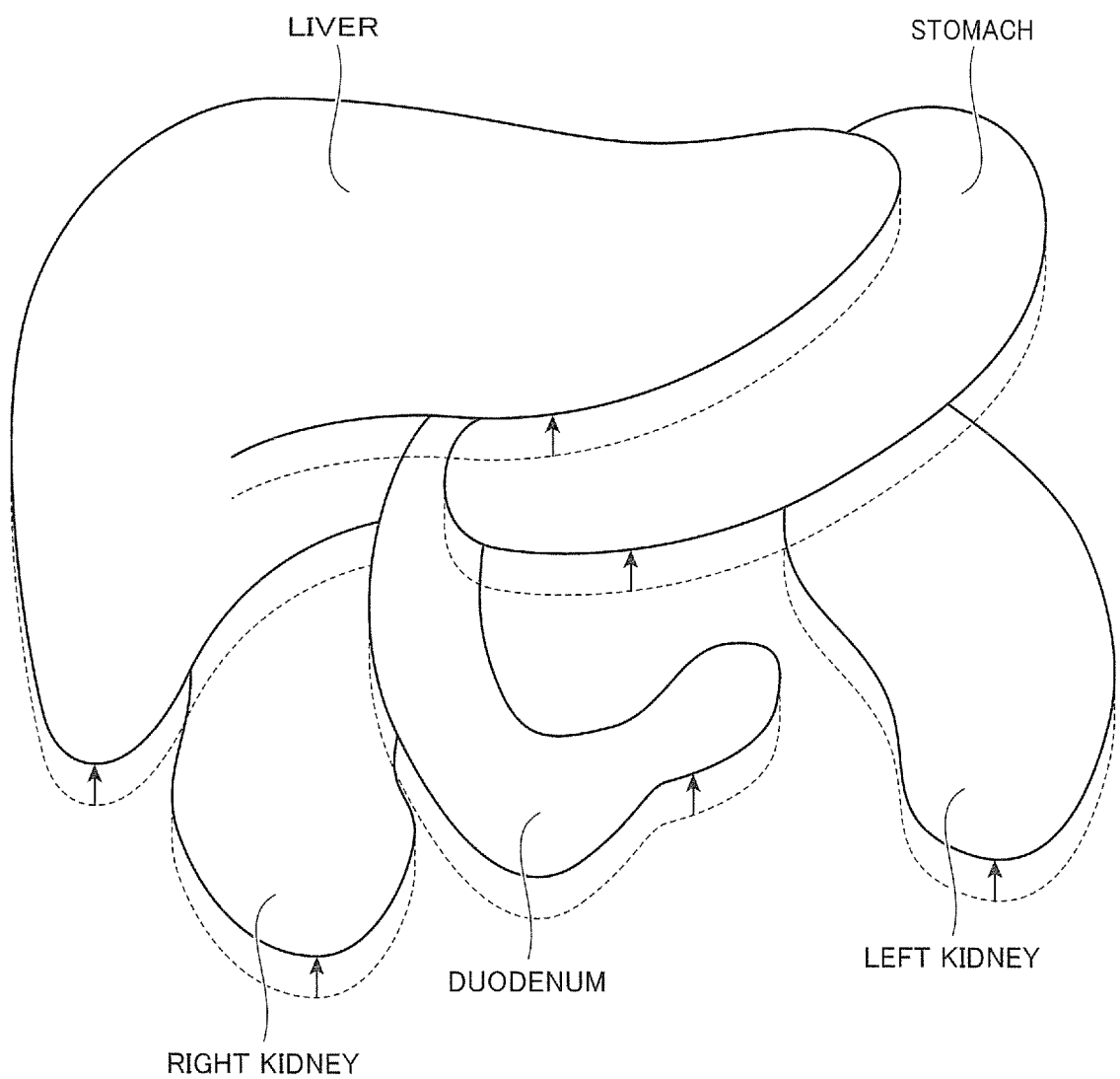
FIG. 25 illustrates estimation of destinations of movement of multiple organs, the movement causing deformation of the organs.

FIG. 25 illustrates estimation of destinations of movement of multiple organs, the movement causing deformation of the organs.

The example in FIG. 25 shows a case of medical image data including the liver, stomach, duodenum, left kidney and right kidney. The image example shown in FIG. 25 is an example, and may include other organs or a smaller number of organs.

The shape and position of organs in the body also change depending on breathing, posture and physical condition in the measurement, and the position moves; however, use of the technique described in Exemplary embodiment 1 makes it possible to estimate the shape and position changes of multiple organs (including tumors) with high accuracy. In other words, in the exemplary embodiment, movement of the position of organs is also learned.

Changes in the shape and position of multiple organs (including tumors) due to breathing, posture and physical condition in the measurement are also examples of deformations by time variation.

In FIG. 25, part of the shape and position before deformation are indicated by broken lines.

The capability of estimating the range of deformations and position changes of the multiple organs with high accuracy can be applied to radiation planning in the radiotherapy.

Exemplary Embodiment 3

In Exemplary embodiment 1, the learned model is provided with the feature amount data generated based on the pre-deformation measurement data to estimate the post-deformation shape; however, it may be possible to estimate the post-deformation shape by providing the feature amount data to the learned model that has learned about individual organs or multiple organs, and to check the estimated shape with medical image data, to thereby automatically extract the position of the organs included in the medical image data by using the image recognition technique.

Figure 26:
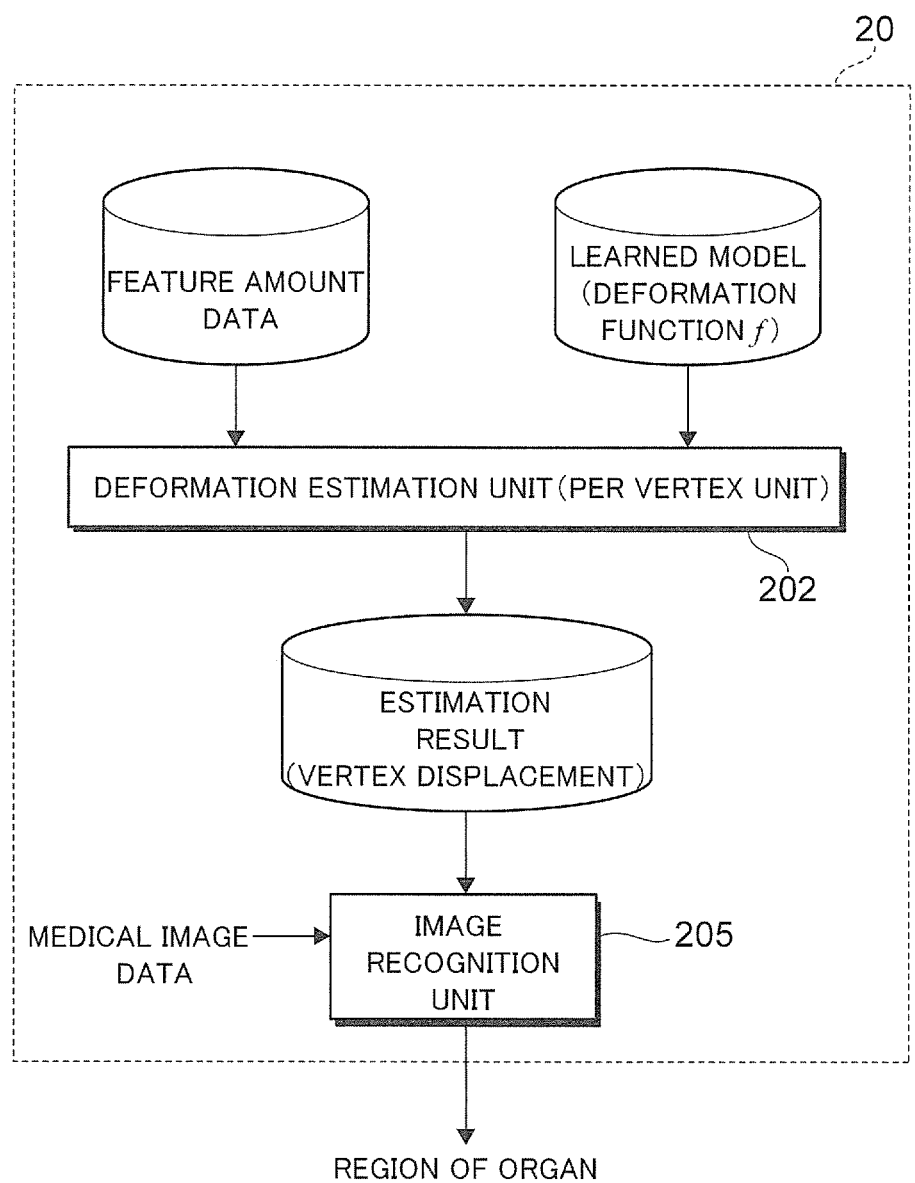
FIG. 26 illustrates the processing function of estimating variations in organ shapes and extracting a region of a specific organ from medical image data.

FIG. 26 illustrates the processing function of estimating the variations in organ shapes and extracting a region of a specific organ from medical image data.

The deformation estimation device 20 can provide the post-deformation shape estimated by the deformation estimation unit 202 to an image recognition unit 205 to check thereof with the medical image data, and can extract the region of the organ to be the target from the medical image data.

Exemplary Embodiment 4

In the above-described exemplary embodiments, description was given of the case in which both measurement data and learned data were three-dimensional data, but there is a possibility that the measurement data is two-dimensional data. For example, the measurement data is given as endoscopic image data.

Figure 27:
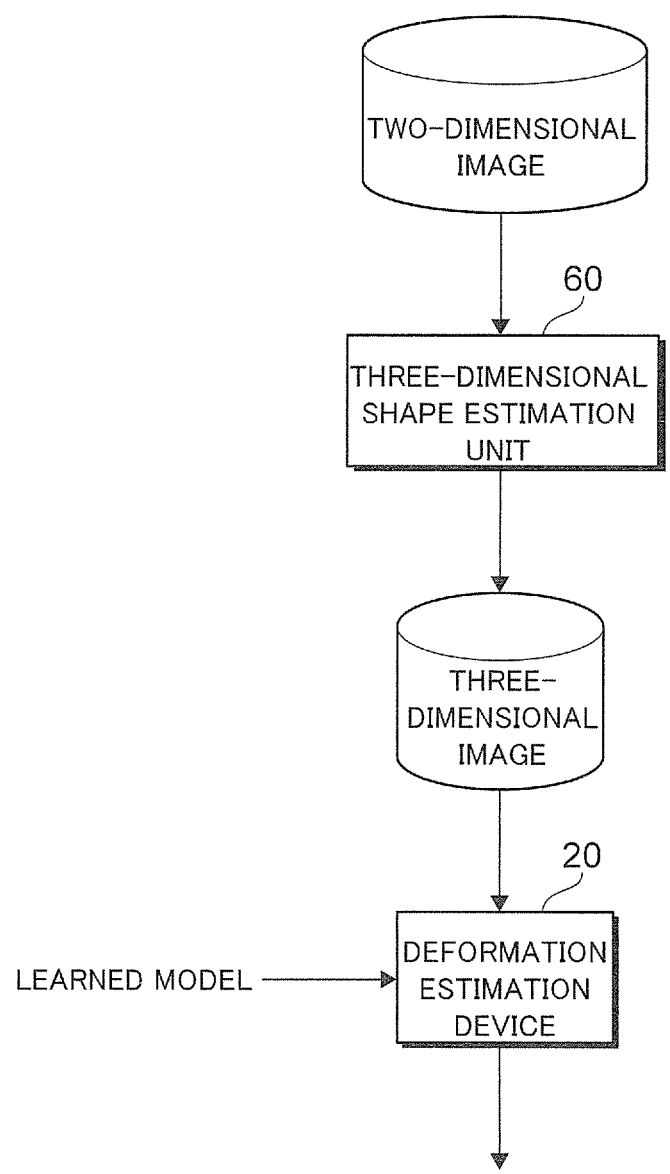
FIG. 27 illustrates an example of estimating the three-dimensional shape from the two-dimensional image data and estimating the deformed shape by use of the estimated three-dimensional shape.

FIG. 27 illustrates an example of estimating the three-dimensional shape from the two-dimensional image data and estimating the post-deformation shape by use of the estimated three-dimensional shape.

In FIG. 27, a two-dimensional image is given as an input, and a three-dimensional image is output by a three-dimensional shape estimation unit 60. For example, the technique of estimating the three-dimensional shape from only the two-dimensional color information is described in the following literature.

H. Fan et al., "A point set generation network for 3D object reconstruction from a single image," CVPR, 2017.

Note that the estimation processing by the three-dimensional shape estimation unit 60 can be achieved by combining the extraction processing of specific organ regions by graph-cutting with the estimation processing using the learned model that has learned by applying machine learning, deep learning, convolutional neural network, and so on.

The learned model shown here has learned and stored the feature amount data $x_i$ including the difference between each micro region and other micro regions $d_{ij}$ in the shape model $M_{(i)I}$ generated from the measurement data of the organ region before deformation, and the relation providing the displacement amount data $y_i$ from each micro region in the shape model $M_{(i)I}$ of the organ region before deformation to the each corresponding micro region in the shape model $M_{(i)D}$ of the organ region after deformation.

Use of the technique of the exemplary embodiment makes it possible not only to estimate the post-deformation shape, but also to estimate the position of the tumor that cannot be seen from the appearance, even in the situation where only two-dimensional image data can be measured.

Exemplary Embodiment 5

In the above-described exemplary embodiments, examples of the candidate for the feature amount data $x_i$ included the coordinates $v_i$ of each vertex i, the gradient or the normal vector $n_i$ defining the micro region, the curvature (second derivative, discrete Laplacian) $l_i$, the difference between vertexes $d_{ij}$, the shrinkage ratio $s_i$ of the micro region, and Voronoi area $r_i$ in the micro region; however, as the candidate for the feature amount data $x_i$, the deviation amount $u_i$ between each micro region and a corresponding region of the average shape model (hereinafter referred to as "average shape model") may be additionally included. In this case, the deviation amount $u_i$ may be used alone as the feature quantity data $x_i$, or in combination with other candidates as the feature amount data $x_i$.

Figure 28:
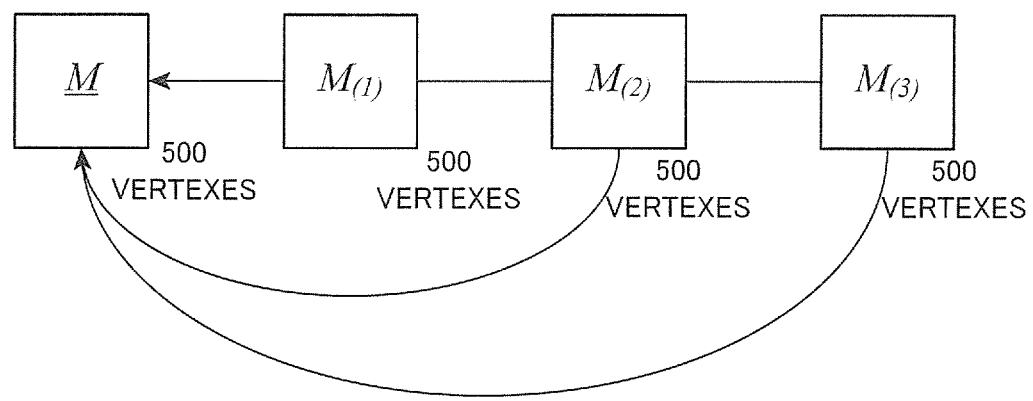
FIG. 28 illustrates an average shape model generated from plural shape models.

FIG. 28 illustrates the average shape model M generated from multiple shape models $M_{(i)}$. The coordinates $v_{Mi}$ of the vertex i in the average shape model $\underline{M}$ are generated, for example, as the average value of the coordinates $v_i$ of the corresponding vertex group in the multiple shape models $M_{(i)}$. In the case of FIG. 28, the average value of the coordinates is calculated for each of the 500 vertexes.

Figure 29:
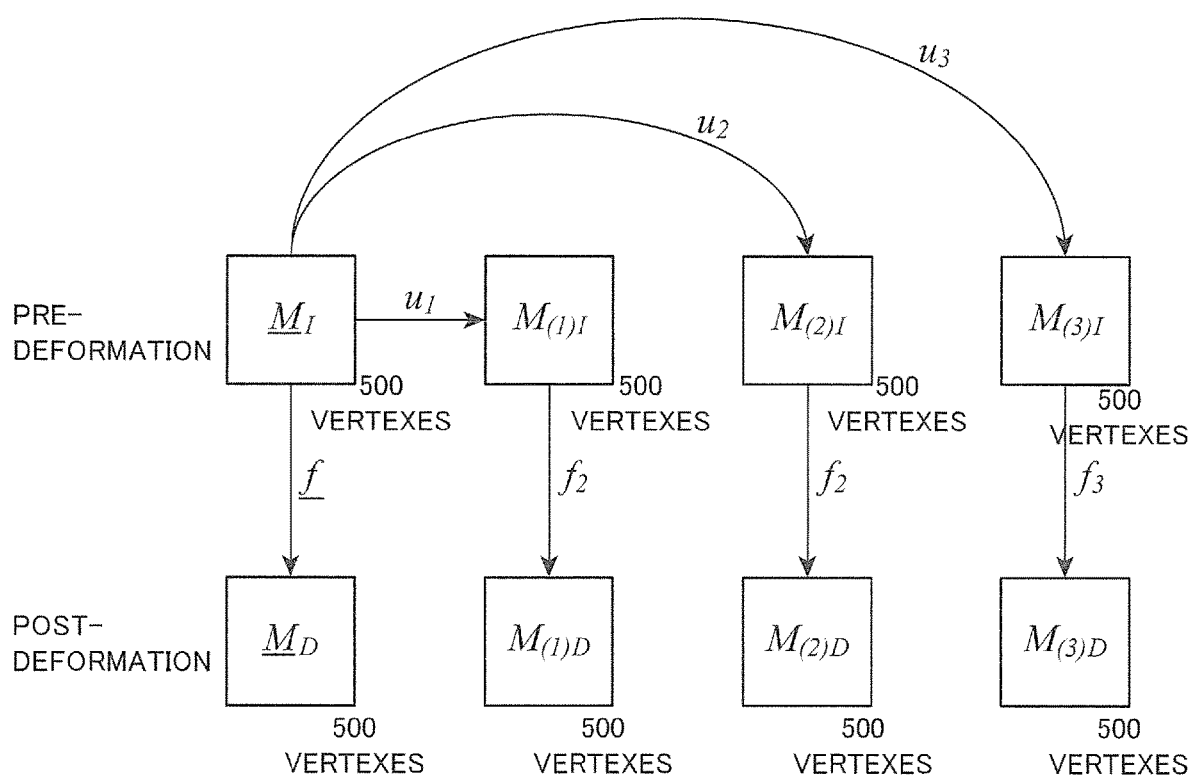
FIG. 29 illustrates amounts of deviations between corresponding regions of the respective shape models with respect to the average shape model.

FIG. 29 illustrates the deviation amounts $u_i$ between corresponding regions of the respective shape models with respect to the average shape model $\underline{M}_I$ before deformation. Here, the corresponding region is the micro region corresponding to the vertex i. Consequently, the deviation amount $u_i$ is calculated for the 500 vertexes. The deformation function $\underline{f}$ in the figure represents the deformation function generating the post-deformation average shape model MD from the pre-deformation average shape model $\underline{M}_I$.

Note that it is also possible to provide the average shape model $\underline{M}$ here as the template shape T and to repeatedly calculate the shape model $M_{(i)}$ corresponding to the shape data $S_{(i)}$.

Exemplary Embodiment 6

In the above-described exemplary embodiments, description was given of the case in which the relation between the feature amount data $x_i$ and the displacement amount data $y_i$ before and after the deformation for the same organ was learned, and the post-deformation shape of any measurement data was estimated by using the learned model, which was the result of learning; however, it may be possible to learn the relation between the deviation amount of an object 1 from the average model and the coordinates vs of each vertex s constituting another object 2 having a constraint with the object 1, and to estimate the position of the object 2 from the measurement data of any object 1 by using the learned model as a result of the learning.

Figure 30:
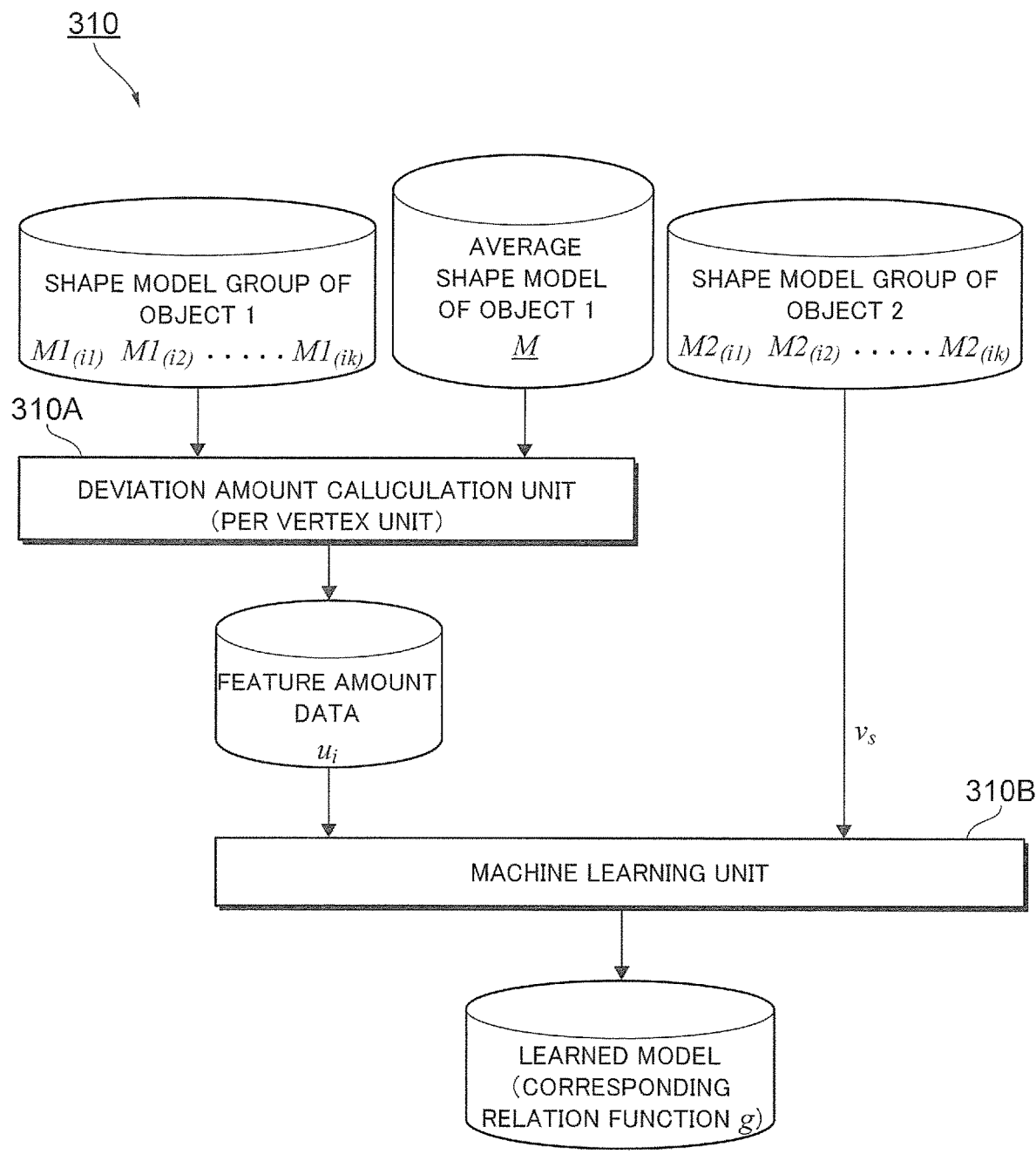
FIG. 30 illustrates a configuration example of a machine learning device that learns a relation between the amounts of deviation between each vertex of the shape model (including the shape model after upsampling) generated from the measurement data of an object 1 and the corresponding vertex of the average shape model, and the coordinates of each vertex constituting another object 2, which has a constraint relation with the object 1.

FIG. 30 illustrates a configuration example of a machine learning device 310 that learns the relation between the deviation amount $u_i$ between each vertex i of the shape models (including the shape models after the upsampling) $M1_{(i1)}$ to $M1_{(ik)}$ generated from the measurement data of the object 1 and the corresponding vertex of the average shape model $\underline{M}$, and the coordinates vs of each vertex s constituting the other object 2, which has a constraint relation with the object 1. Note that, similar to the above-described exemplary embodiments, the machine learning device 310 is implemented through execution of programs by a computer.

The machine learning device 310 includes a deviation amount calculation unit 310A calculating and outputting a deviation amount $u_i$ per each vertex, and a machine learning unit 310B learning the relation between each deviation amount $u_i$ and the coordinates vs of each vertex s of object 2. In the case of the example, the machine learning unit 310B outputs the corresponding relation function g as a result of the learning.

For example, the object 1 is the liver and the object 2 is the pancreas. The constraint relation here is, for example, adjacent or connected relation. In the case where the object 1 is the liver, the adjacent objects 2 are the stomach, duodenum, and right kidney; the connecting objects 2 are the duodenum, pancreas, spleen, and so on.

Figure 31:
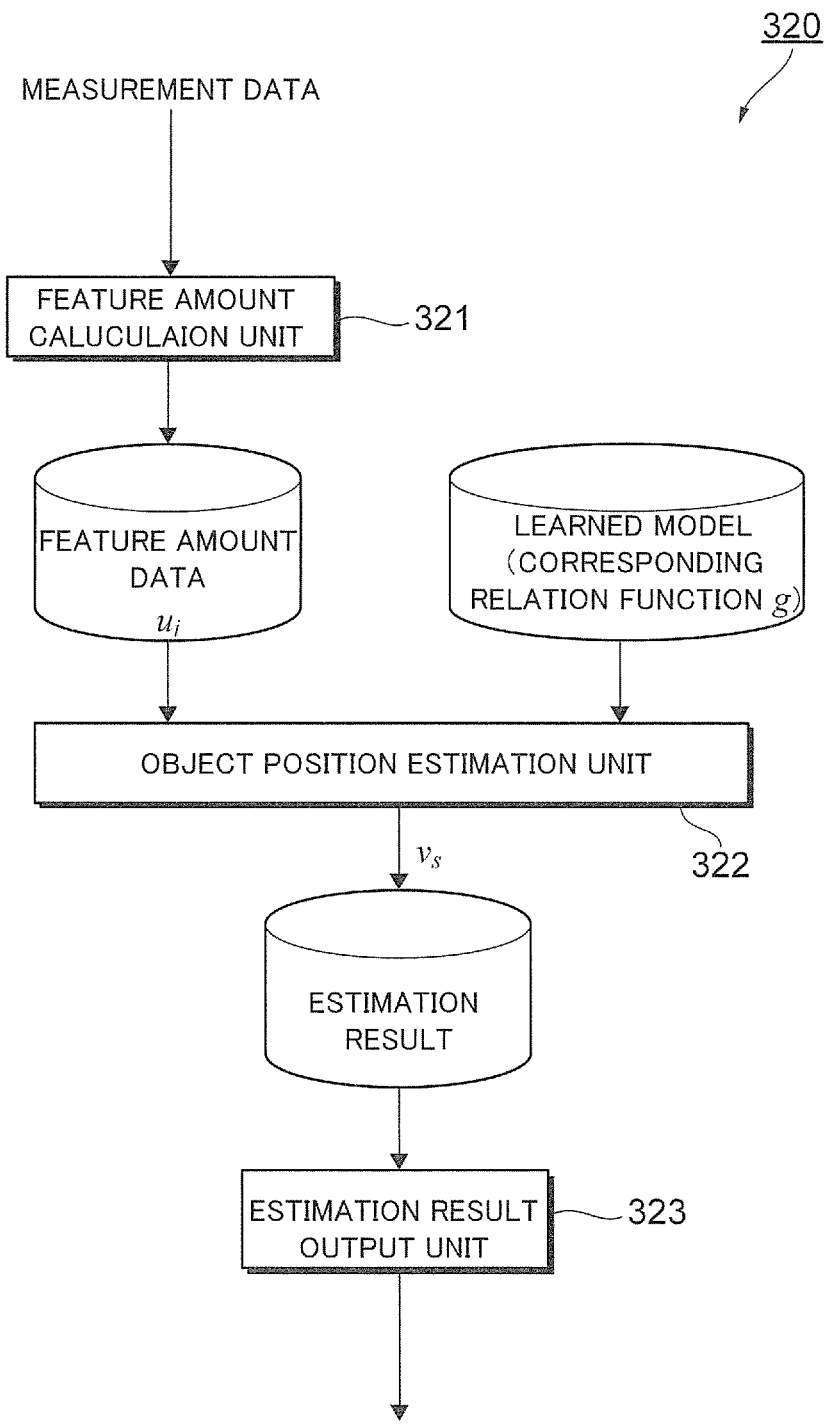
FIG. 31 illustrates a configuration example of a position estimation device that estimates the position of the object 2 from the amount of deviation between the shape model generated from the measurement data of the object 1 and the average model.

FIG. 31 illustrates a configuration example of a position estimation device 320 that estimates the position vs of the object 2 from the deviation amount $u_i$ between the shape model generated from the measurement data of the object 1 and the average model.

The deformation estimation device 320 includes: a feature amount calculation unit 321 calculating, as the feature amount data, the deviation amount $u_i$ of each vertex i constituting the shape model generated from the measurement data of the object 1 from the average shape model M; an object position estimation unit 322 applying the calculated deviation amount $u_i$ to the learned model to estimate the position of the object 2; and an estimation result output unit 323 outputting the estimation results.

Similar to the above-described exemplary embodiments, the position estimation device 320 is also implemented through execution of programs by a computer.

Exemplary Embodiment 7

In the above exemplary embodiments, description was given of the learning of deformation of an entire object using image data captured or measured the entire object; however, the following description will be given of learning of deformation of an entire object using image data captured or measured a part of the object.

In the following description, three-dimensional image data generated by cone-beam CT is used as an example of the image data captured or measured a part of an object. The cone-beam CT can generate three-dimensional image data of a subject by simply rotating once a movable device configured with an irradiator irradiating the subject with a beam of X-rays in a cone shape or quadrangular-pyramid shape and a two-dimensional detector detecting X-rays having passed through the subject.

For this reason, the cone-beam CT is used, for example, to capture an image of a lung during surgery. However, the volume of lung parenchyma included in the image-capturing scope of the cone-beam CT is less than half the overall lung volume in some cases, and it is not clear which region is captured.

Figure 32A:
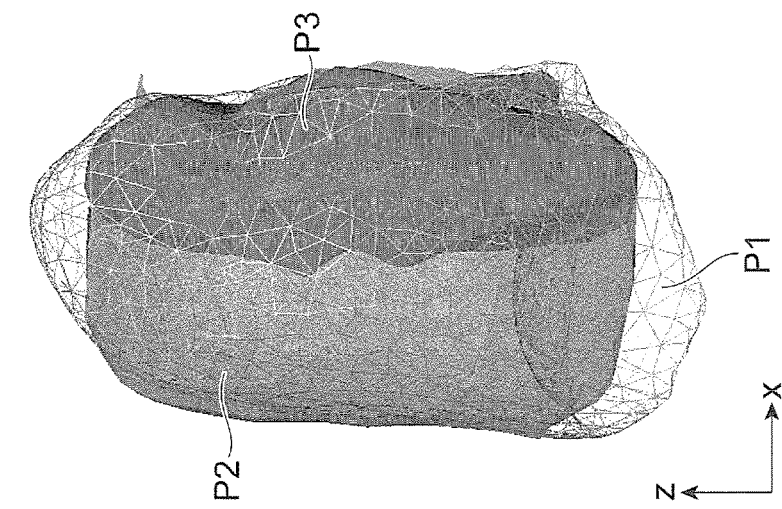
FIGS. 32A to 32C illustrate a relation between the CT image of the right lung captured with cone-beam CT and the CT image of the same right lung captured with CT, where
Figure 32B:
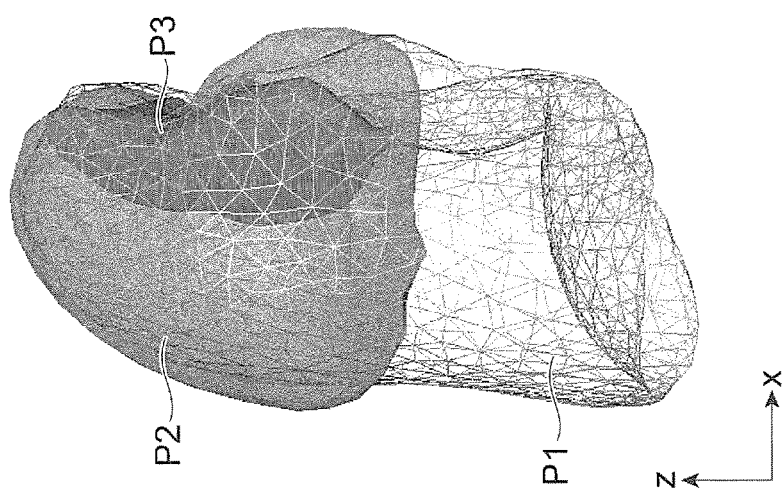
Figure 32C:
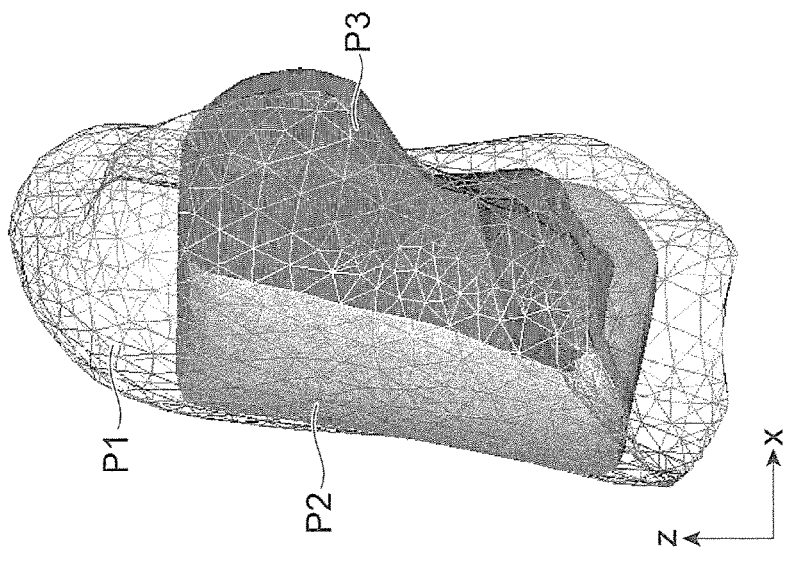

FIGS. 32A to 32C illustrate a relation between the CT image of the right lung captured with cone-beam CT and the CT image of the same right lung captured with CT. FIG. 32A shows the CT images of a specimen A, FIG. 32B shows the CT images of a specimen B, and FIG. 32C shows the CT images of a specimen C;

In the figure, the CT image P1, which has the largest area shown by a mesh, is the CT image captured before the surgery. Unlike the cone-beam CT capturing only a partial image of the lung, the entire lung image is captured. Since the lung is before surgery, the lung is in the aerated condition. The CT image P1 here corresponds to the pre-deformation image $I_{(i)I}$ in Exemplary embodiment 1.

In the figure, the CT image P2 having the second largest area with a light color is the CT image captured with the cone-beam CT during the surgery. The CT image P2 shows a part of the lung that is in the aerated condition. For any of the specimens A, B, and C, the CT image P2 is a smaller area than the CT image P1.

In the figure, the CT image P3 having the smallest area with a dark color is also the CT image captured with the cone-beam CT during the surgery. The CT image P3 shows a part of the lung that is in the deaerated condition. Consequently, in any of the specimens A, B, and C, the CT image P3 is a smaller region than the CT image P2.

As described above, in the exemplary embodiment, description will be given of the case in which the CT images P2 and P3 are used to learn deformation of the entire lung. However, mere learning of deformation between the CT images P2 and P3, which are the partial images, is performed, the results of the learning cannot be reflected in the learning of the deformation of the entire lung.

Hence, in the exemplary embodiment, deformation between the partial images is learned as variation in a part of the entire lung by alignment with the CT image P1 of the entire lung that was captured before surgery.

Figure 33:
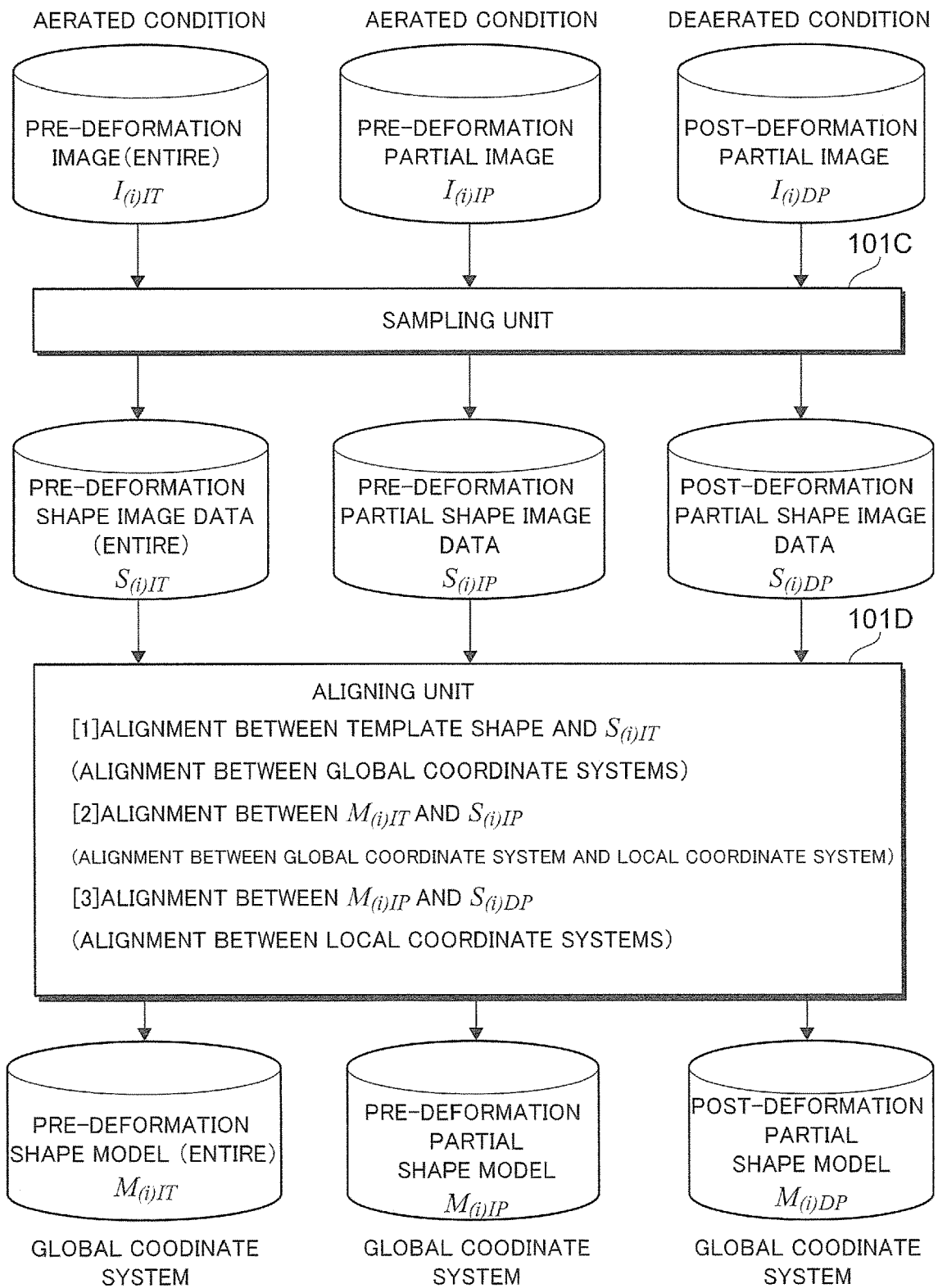
FIG. 33 shows an example of processing executed in the shape model generation unit used in Exemplary embodiment 7.

FIG. 33 shows an example of processing executed in the shape model generation unit 101 (refer to FIG. 3) used in Exemplary embodiment 7. In FIG. 33, components corresponding to those of FIG. 5 are provided with same reference signs.

Note that the hardware configuration and the functional configuration of the machine learning device are similar to those of Exemplary embodiment 1. In other words, the machine learning device in Exemplary embodiment 7 also generates a shape model for each of the pre-deformation image $I_{(i)I}$ and the post-deformation image $I_{(i)D}$, and thereafter, upsamples the generated shape model and then executes learning per micro region unit.

In the case of FIG. 33, two types of images are prepared as the pre-deformation image. One of the images is the pre-deformation image $I_{(i)IT}$ captured the entire lung in the aerated condition before surgery, and the other is the pre-deformation image $I_{(i)IP}$ captured a part of the lung in the aerated condition during surgery. As the post-deformation image, the post-deformation partial image $I_{(i)DP}$ captured a part of the lung in the deaerated condition during surgery is used.

First, the sampling unit 101C samples each of the pre-deformation image $I_{(i)IT}$, the pre-deformation partial image $I_{(i)IP}$, and the post-deformation partial image $I_{(i)DP}$ to generate shape data of the voxel mesh structure or the polygon mesh structure. Here, the shape data corresponding to the pre-deformation image $I_{(i)IT}$ is referred to as $S_{(i)IT}$, the shape data corresponding to the pre-deformation partial image $I_{(i)IP}$ is referred to as $S_{(i)IP}$, and the shape data corresponding to the post-deformation partial image $I_{(i)D}$ is referred to as $S_{(i)D}$.

As described in Exemplary embodiment 1, the size of the pre-deformation image and the post-deformation image also differs depending on differences in the specimens and the image capturing conditions. In addition, the size of the pre-deformation image and the post-deformation image differs between the CT used for pre-surgical image capturing and the cone-beam CT used during surgery. In addition, there are limitations to unify the position and physical condition of the specimens during image capturing.

For this reason, as described in Exemplary embodiment 1, the number of vertexes of the voxels included in the independently-generated shape data is inconsistent in general.

Consequently, in the case of the exemplary embodiment, the generated shape data is aligned with the template shape T to generate the shape model M with the aligned number of vertexes. In FIG. 33, the alignment unit 101D executes the alignment.

First, by using the template shape T corresponding to the entire right lung, the alignment unit 101D aligns the number of vertexes in the pre-deformation shape data $S_{(i)IT}$ corresponding to the entire right lung with the same number of vertexes as the template shape T. The details of the processing are the same as those of Exemplary embodiment 1. For example, the pre-deformation shape model $M_{(i)IT}$ with 500 vertexes is generated.

This alignment is the alignment between the global coordinate systems.

Next, the alignment unit 101D uses the generated pre-deformation shape model $M_{(i)IT}$ corresponding to the entire right lung as a template shape to align the pre-deformation partial shape data $S_{(i)IP}$ corresponding to a part of the right lung of the same specimen. As a result, the pre-deformation partial shape model $M_{(i)IP}$ corresponding to the pre-deformation partial shape data $S_{(i)IP}$ is generated. Of course, the number of vertexes constituting the pre-deformation partial shape model $M_{(i)IP}$ is less than the number of vertexes in the template shape.

The site and volume to be captured by the cone-beam CT are, as shown in FIGS. 32A to 32C, different by each specimen and each time of image capturing. For this reason, the number of vertexes constituting the pre-deformation partial shape model $M_{(i)IP}$ differs by each partial image.

This alignment is the alignment between the global coordinate system and the local coordinate system.

Next, the alignment unit 101D uses the generated pre-deformation shape model $M_{(i)IP}$ corresponding to a part of the right lung in the aerated condition as a template shape to align the post-deformation partial shape data $S_{(i)DP}$ corresponding to a part of the right lung in the deaerated condition of the same specimen. As a result, the post-deformation partial shape model $M_{(i)DP}$ corresponding to the post-deformation partial shape data $S_{(i)DP}$ is generated. However, the number of vertexes constituting the post-deformation partial shape model $M_{(i)DP}$ is the same as the number of vertexes of the pre-deformation partial shape model $M_{(i)IP}$ used as the template shape.

This alignment is the alignment between the local coordinate systems.

FIGS. 34A to 34D illustrate the results of alignment of the CT image P2 (namely, the pre-deformation partial shape model) of the lung in the aerated condition captured with the cone-beam CT and the CT image P3 (namely, the post-deformation partial shape model) of the same lung in the deaerated condition captured with the cone-beam CT. FIG. 34A shows the shape model of a specimen A, FIG. 34B shows the shape model of a specimen B, FIG. 34C shows the shape model of a specimen C, and FIG. 34D shows the results of the alignment. Incidentally, the CT images P2 and P3 correspond to the partial images in FIGS. 32A to 32C.

In the case of the specimen A shown in FIG. 34A, the mean distance (MD) between the corresponding vertexes between the CT image P2 (pre-deformation partial shape model) deformed into the shape of the CT image P3 (post-deformation partial shape model) and the CT image P3 (post-deformation partial shape model) is 0.21 mm, and the maximum distance (Hausdorff distance: HD) between corresponding vertexes is 0.98 mm. In the case of FIGS. 34A to 34D, the mean distance between the corresponding vertexes is calculated as the distance between the vertexes of the image after the CT image P2 is deformed into the shape of CT image P3 (vertexes are derived from the CT image P2) and the corresponding adjacent surface of the CT image P3. The adjacent surface is, for example, the position on the CT image P3 closest to the vertex of the CT image P2.

The degree of inclusion (dice similarity distance: DSC) between the estimated values and true values of the vertex group is 98.93%.

The MD of the specimen B is 0.15 mm, the HD is 0.79 mm, and the DSC is 99.24%. The MD of the specimen C is 0.23 mm, the HD is 1.30 mm, and the DSC is 98.94%.

As shown in FIGS. 34A to 34D, the pre-deformation partial shape model $M_{(i)IP}$ is aligned with the post-deformation shape model $M_{(i)DP}$ with high accuracy.

FIG. 35 explains results of alignment of the CT image P1 (pre-deformation shape model) of the lung in the aerated condition of the specimen captured with CT with the template shape T of the lung. In this case, each value was calculated between the corresponding vertexes of the image generated by deforming the template shape T of the lung to match the image P1 (pre-deformation shape model) and the CT image P1 (pre-deformation shape model).

In the case of FIG. 35, the MD of the specimen A is 0.33 mm, the HD is 1.91 mm, and the DSC is 98.14%. The MD of the specimen B is 0.54 mm, the HD is 2.26 mm, and the DSC is 97.94%. The MD of the specimen C is 0.39 mm, the HD is 1.53 mm, and the DSC is 98.31%.

As shown in FIG. 35, the template shape T is aligned with high accuracy with the shape data of CT image P1 of the entire lung independently captured for each specimen.

Figure 36:
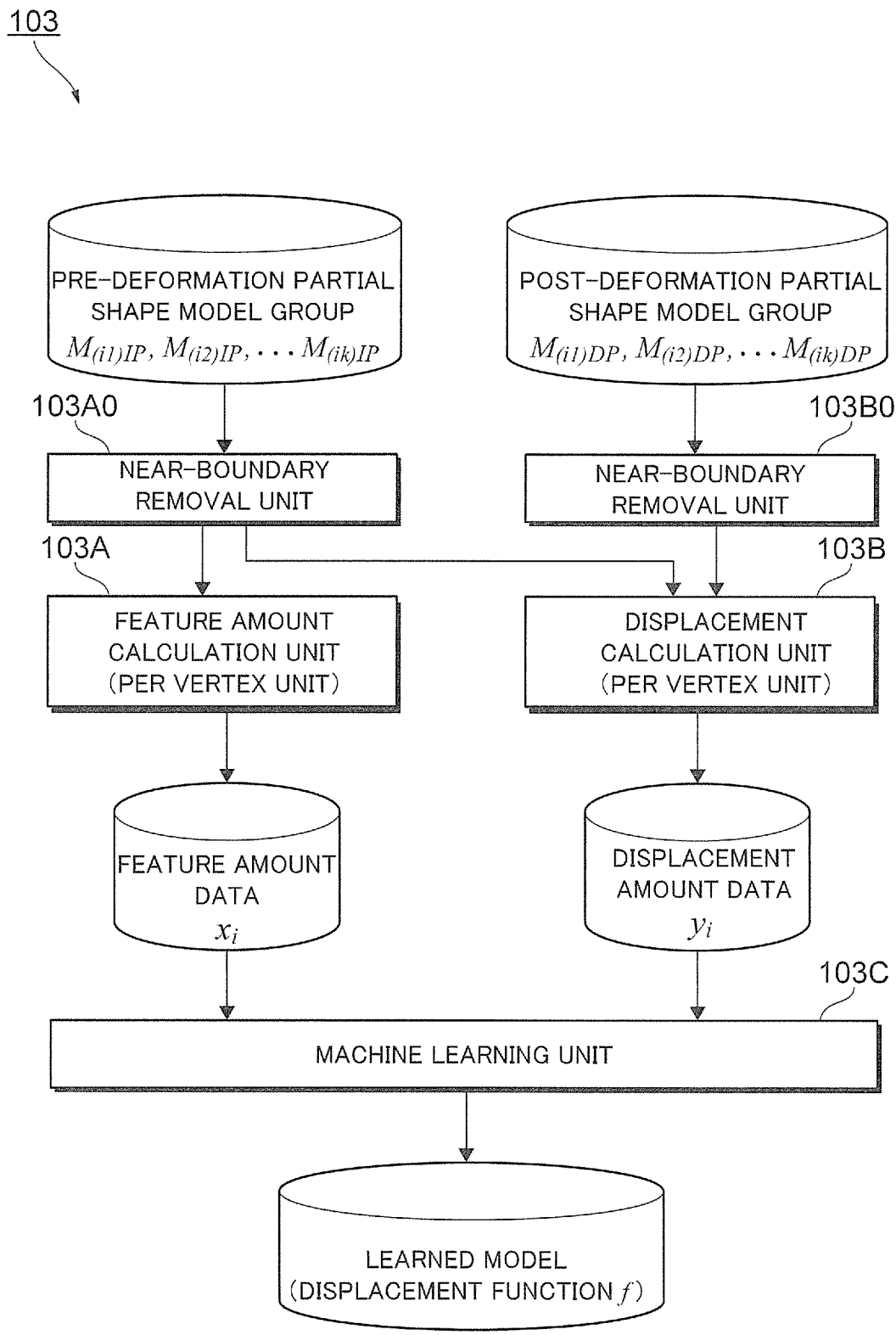
FIG. 36 shows an example of processing executed in the deformation learning unit used in Exemplary embodiment 7.

FIG. 36 shows an example of processing executed in the deformation learning unit 103 (refer to FIG. 3) used in Exemplary embodiment 7. In FIG. 36, components corresponding to those of FIG. 14 are provided with same reference signs.

The pre-deformation partial shape model group $M_{(i1)IP}, \ldots, M_{(ik)IP}$ is a model group generated by upsampling the pre-deformation partial shape model $M_{(i)IP}$. The post-deformation partial shape model group $M_{(i1)DP}, \ldots, M_{(ik)DP}$ is a model group generated by upsampling the post-deformation partial shape model $M_{(i)DP}$.

In the case of Exemplary embodiment 1, the feature amount per vertex unit is calculated directly from the model group generated by upsampling; however, in the exemplary embodiment, the vertexes near the boundary are removed in advance by using near-boundary removal units 103A0 and 103B0. The partial images captured with cone-beam CT have low reliability near the boundary thereof with the region of the entire lung that was not captured.

Figure 37A:
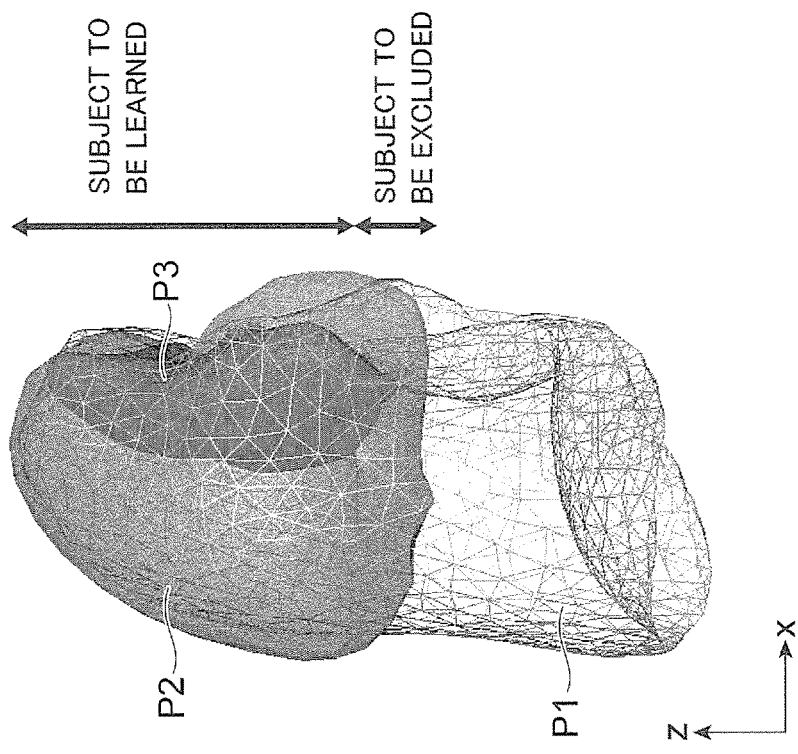
FIGS. 37A and 37B illustrate a subject used for learning (a subject to be learned) and a subject not used for learning (a subject to be excluded), where
Figure 37B:
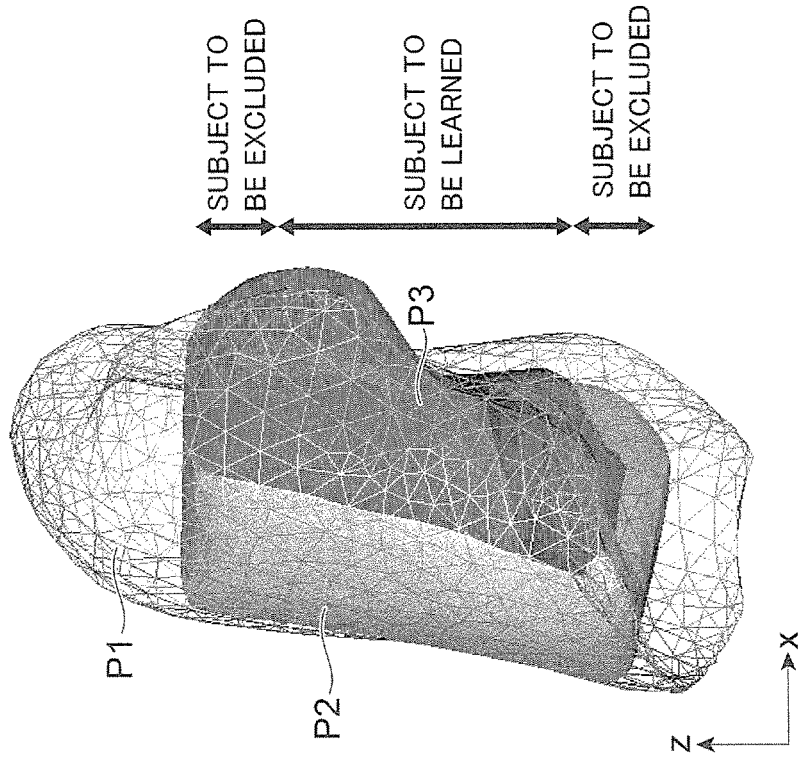

FIGS. 37A and 37B illustrate a subject used for learning (a subject to be learned) and a subject not used for learning (a subject to be excluded). FIG. 37A shows the shape model of a specimen A, and FIG. 37B shows the shape model of a specimen B.

In the case of FIG. 37A, in the specimen A, the vicinity of the center of the lung is captured with the cone-beam CT, but the upper and lower portions of the lung are not captured. Consequently, the boundaries appear in two locations: The upper end side and the lower end side of the CT image P2 (pre-deformation partial shape model) and the CT image P3 (post-deformation partial shape model).

On the other hand, in the specimen B, the upper half of the lung is captured with the cone-beam CT, but the lower half of the lung is not captured. Consequently, the boundary appears only at one location: The lower end side of the CT image P2 (pre-deformation partial shape model) and the CT image P3 (post-deformation partial shape model).

In the exemplary embodiment, the range of 10 mm from each boundary is excluded from the subject to be learned. Note that the value is merely an example. However, the vertexes to be excluded from the subject to be learned may be determined by the ratio (%) of the number of vertexes constituting the shape model, not by the distance from the boundary. For example, 10% can be used.

Let us return to the description of FIG. 36. The near-boundary removal unit 103A0 removes the vertexes existing near the boundary from each of the models in the pre-deformation partial shape model group $M_{(i1)IP}, \ldots, M_{(ik)IP}$. The group of remaining vertexes (namely, the group of vertexes to be learned) is outputted to the feature amount calculation unit 103A and the displacement calculation unit 103B.

On the other hand, the near-boundary removal unit 103B0 removes the vertexes existing near the boundary from each of the models in the post-deformation partial shape model group $M_{(i1)DP}, \ldots, M_{(ik)DP}$. The group of remaining vertexes (namely, the group of vertexes to be learned) is outputted to the displacement calculation unit 103B.

FIGS. 38A to 38C illustrate the displacement amount data $y_i$ in the case where the vertexes near the boundary are not removed. FIG. 38A shows the displacement amount data $y_i$ that appears in the x-y plane and the displacement amount data $y_i$ that appears in the x-z plane of a specimen A, FIG. 38B shows the displacement amount data $y_i$ that appears in the x-y plane and the displacement amount data $y_i$ that appears in the x-z plane of a specimen B, and FIG. 38C shows the displacement amount data $y_i$ that appears in the x-y plane and the displacement amount data $y_i$ that appears in the x-z plane of a specimen C.

FIGS. 39A to 39C illustrate the displacement amount data $y_i$ in the case where the vertexes near the boundary are removed. FIG. 39A shows the displacement amount data $y_i$ that appears in the x-y plane and the displacement amount data $y_i$ that appears in the x-z plane of a specimen A, FIG. 39B shows the displacement amount data $y_i$ that appears in the x-y plane and the displacement amount data $y_i$ that appears in the x-z plane of a specimen B, and FIG. 39C shows the displacement amount data $y_i$ that appears in the x-y plane and the displacement amount data $y_i$ that appears in the x-z plane of a specimen C.

In all the figures, the length of the displacement amount data $y_i$ is shorter than it is in the actuality, taking the visibility into consideration.

The displacement amount data $y_i$ representing the displacement before and after the deformation of each vertex to be learned is calculated by the displacement calculation unit 103B (refer to FIG. 36). In addition, the feature amount data $x_i$ of each vertex to be learned is calculated by the feature amount calculation unit 103A (refer to FIG. 36).

The calculated feature amount data $x_i$ and displacement amount data $y_i$ are given to the machine learning unit 103C (refer to FIG. 36). Thereafter, the machine learning unit 103C learns the deformation function f representing the relation of the feature amount data $x_i$ and the displacement amount data $y_i$ between the corresponding vertexes. Note that the subject of the partial image captured by the cone-beam CT is the patient during surgery. For this reason, the partial image captured with the cone-beam CT reflects the gravitational deformation in accordance with the patient's posture (namely, the lateral position) during surgery. As a result, the learned model generated by the machine learning unit 103C also reflects the gravitational deformation.

Figure 40A:
FIGS. 40A and 40B illustrate the deformed shape PS estimated by inputting the CT data captured prior to surgery into the learned model learned by use of partial images captured with the cone-beam CT during surgery, where
Figure 40B:
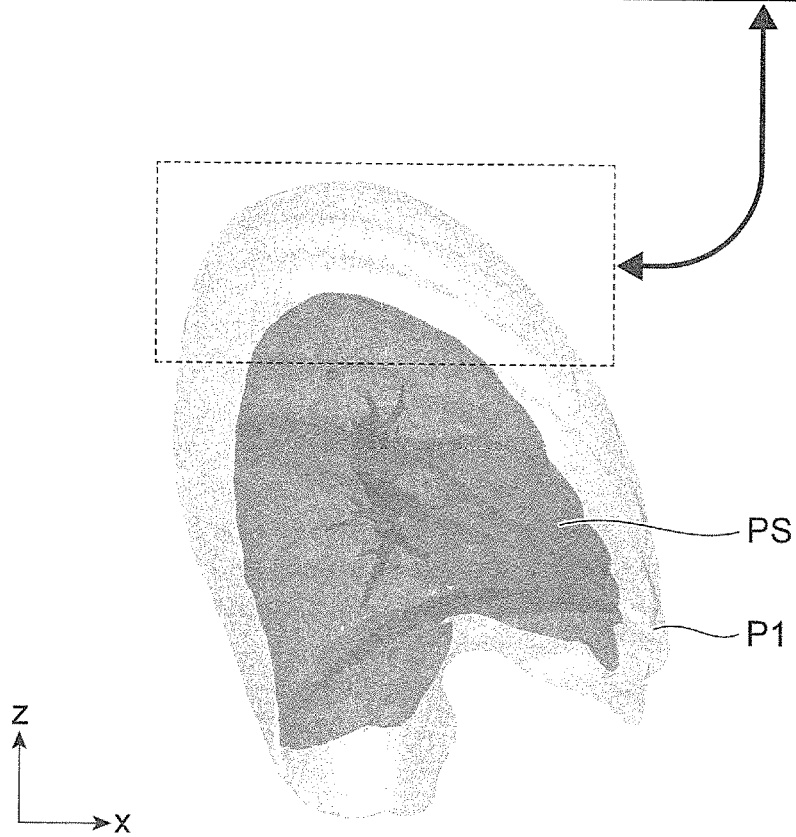

FIGS. 40A and 40B illustrate the post-deformation shape PS estimated by inputting the CT data captured prior to surgery into the learned model that has learned by use of the partial image captured with the cone-beam CT during surgery. FIG. 40A shows the actual surgical image, and FIG. 40B shows the estimated shape PS.

As shown in FIGS. 40A and 40B, it is confirmed that the post-deformation shape PS estimated from the CT data captured before surgery is deformed in the direction of gravitational force in the lateral position (namely, in the direction close to the heart), and appearance similar to the surgical image is acquired.

Figure 41:
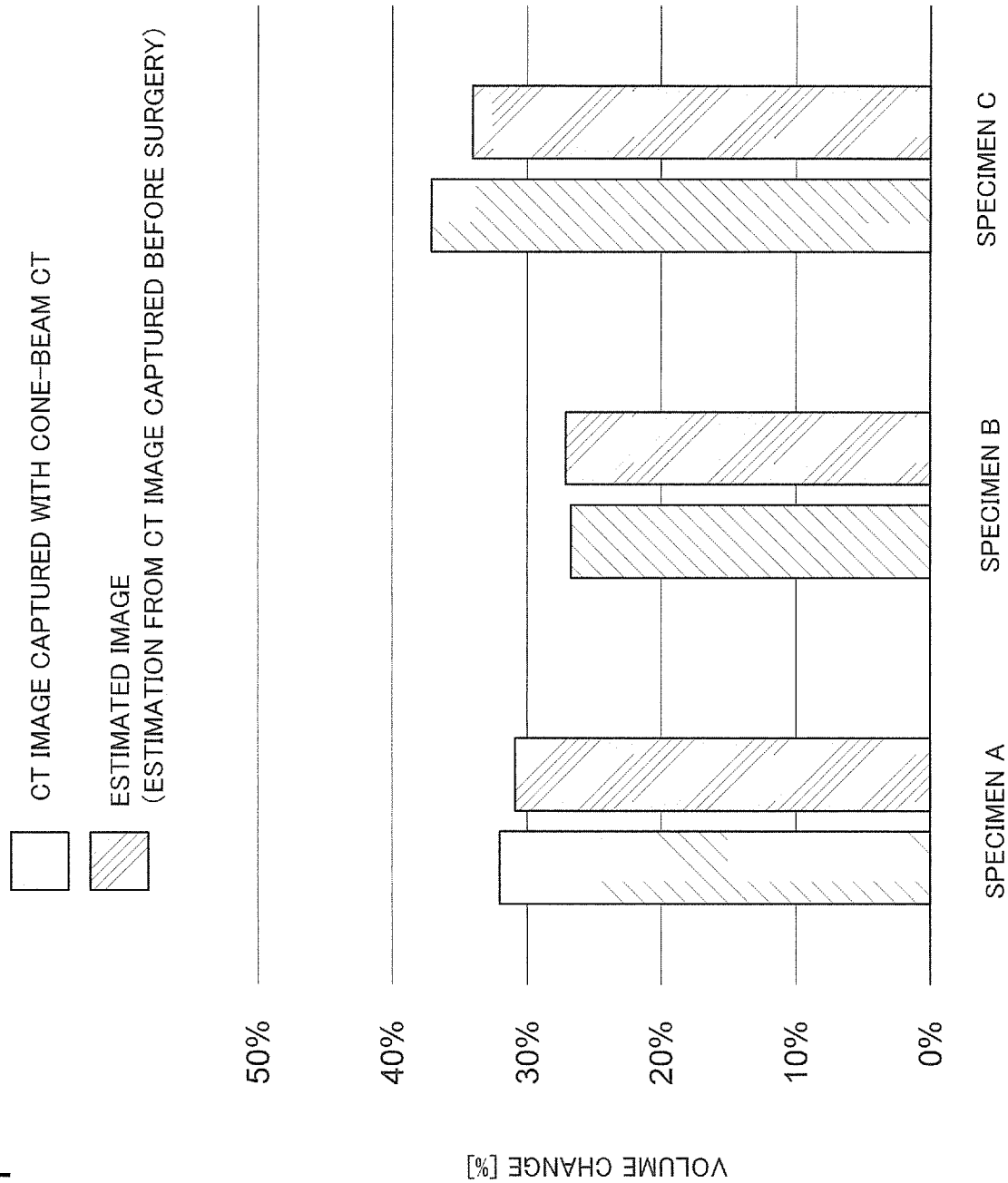
FIG. 41 illustrates the accuracy of the estimated image using the learned model generated by the technique described in Exemplary embodiment 7.

FIG. 41 illustrates the accuracy of the estimated image using the learned model generated by the technique described in Exemplary embodiment 7.

The vertical axis in the figure indicates the changes in lung volume before and after surgery, and the horizontal axis indicates the specimen. FIG. 41 contrastively shows the change in volume before and after the deformation of the estimated image in the exemplary embodiment assuming that the change in volume before and after the deformation of the CT image captured with the cone-beam CT during surgery is the true value. The estimated image as the three-dimensional image data is, as described above, estimated from the CT image captured before surgery. It has been confirmed that, in any specimen, estimation can be carried out with the error of about 4%. In this way, as described in the exemplary embodiment, even in the case where the deformation is learned using the partial images, the deformation of an entire object can be estimated with high accuracy.

Note that, in the above description, the cone-beam CT is used for acquiring the partial image; however, the device for acquiring the partial image is not limited to the cone-beam CT.

Other Exemplary Embodiments

So far, the exemplary embodiments according to the present invention have been described, but the technical scope of the present invention is not limited to the scope described in the above-described exemplary embodiments.

It is obvious from the following claims that various modifications and improvements added to the above-described exemplary embodiment are also included in the technical scope of the present invention.

For example, in the above exemplary embodiments, a single vertex is assumed as the micro region, but multiple vertexes may be included.

Moreover, in the above exemplary embodiments, the learned model is generated by learning the relation between the feature amount data and the displacement amount data for each vertex by using the kernel regression model; however, it may also be possible to generate the learned model by using the deep learning or the convolutional neural network.

In addition, in the above exemplary embodiments, the relation of distance between the vertexes constituting the shape model is not particularly defined, but may be constrained to be equally spaced.

In the above exemplary embodiments, the learned model is generated by learning the organ before and after deformation exclusively based on the medical image data; however, the technology according to the present invention is not limited to the medical image data.

In the example shown in FIG. 1, the measurement data is inputted from the terminal 50 to the deformation estimation device 20, and the estimation results for the measured data are outputted to the terminal 50. However, the user's evaluation of the measurement data and the estimation results may be given to the machine learning device 10 to be used to update the learned model. In this case, estimation result highly rated by the user is highly rewarded, while estimation result poorly rated by the user is given no reward or poorly rewarded. This type of learning corresponds to the technique of reinforcement learning. Note that the reward may be given by a value of three levels or more in the case of the multilevel evaluation, not only two levels; either 0 or 1.

REFERENCE SIGNS LIST

1: Estimation system
10: Machine learning device
20: Deformation estimation device
30: Database
40: Network
50: Terminal
60: Three-dimensional shape estimation unit
101: Shape model generation unit
101A: Sampling unit
101B: Alignment unit
102: Model upsampling unit
103: Deformation learning unit
103A: Feature amount calculation unit 103B: Displacement calculation unit
103C: Machine learning unit
201: Feature amount calculation unit
202: Deformation estimation unit
203: Estimation result output unit
205: Image recognition unit
300: Output screen
301: Observation image section
302: Estimation image section

The invention claimed is:

1. A machine learning device comprising:
a generation unit generating a first shape model representing a shape of an object before deformation and a second shape model representing a shape of the object after the deformation based on measurement data before and after the deformation; and
a learning unit learning a feature amount including a difference value between each micro region and another micro region that constitute the first shape model, and a relation providing a displacement from the each micro region of the first shape model to each corresponding micro region of the second shape model.

2. The machine learning device according to claim 1, wherein,
when the generation unit generates a third shape model with a change in positions of vertexes, which are elements of the first shape model, and a fourth shape model with a change in positions of vertexes, which are elements of the second shape model,
the learning unit also learns a feature amount including a difference value between each micro region and another micro region that constitute the third shape model, and a relation providing a displacement from the each micro region of the third shape model to each corresponding micro region of the fourth shape model.

3. The machine learning device according to claim 1, wherein the feature amount is defined by at least one of coordinates giving each micro region, a gradient or a normal vector defining each micro region, a curvature defining each micro region, Voronoi area of each micro region, a shrinkage ratio of each micro region, and a deviation amount between each micro region and a corresponding region of an average shape model.

4. The machine learning device according to claim 1, wherein the difference value giving the feature amount is calculated with the micro regions of at least 5% of total micro regions constituting the first shape model.

5. The machine learning device according to claim 1, wherein the learning unit learns the relation by using a kernel regression model.

6. The machine learning device according to claim 1, wherein the measurement data before and after the deformation is medical image data.

7. The machine learning device according to claim 6, wherein the deformation is deaerated deformation of a lung, medical image data of a lung of a patient having treated pneumothorax is used as the measurement data before the deformation due to deaeration, and medical image data of the lung of the patient before treatment of pneumothorax is used as the measurement data after the deformation due to deaeration.

8. The machine learning device according to claim 6, wherein the deformation includes deformation of an organ or movement of a position of an organ due to breathing, time variation, or differences in specimens.

9. The machine learning device according to claim 1, wherein the first shape model and the second shape model are three-dimensional vertex models.

10. The machine learning device according to claim 1, wherein
the first shape model and the second shape model are three-dimensional vertex models, and the difference value between each micro region and another micro region is a difference between vertexes.

11. A non-transitory computer readable medium storing a program causing a computer to execute:
a function of generating a first shape model representing a shape of an object before deformation and a second shape model representing a shape of the object after the deformation based on measurement data before and after the deformation; and
a function of learning a feature amount including a difference value between each micro region and another micro region of the first shape model, and a relation providing a displacement from the each micro region of the first shape model to each corresponding micro region of the second shape model.

12. An estimation device comprising:
an estimation unit, when any measurement data is given, using a learned model having learned a feature amount including a difference value between each micro region and another micro region in a first shape model generated from measurement data before deformation, and a relation providing a displacement from the each micro region of the first shape model to each corresponding micro region of a second shape model after the deformation, to thereby estimate a shape after the deformation corresponding to the any measurement data.

13. The estimation device according to claim 12, wherein the estimation unit calculates a feature amount including a difference value between a micro region and another micro region of a shape model generated for the inputted measurement data, and estimates a displacement of a feature amount corresponding to each micro region by interpolating a relation stored in the learned model.

14. A non-transitory computer readable medium storing a program causing a computer to execute:
a function of, when any measurement data is given, using a learned model having learned a feature amount including a difference value between each micro region and another micro region in a first shape model generated from measurement data before deformation, and a relation providing a displacement from the each micro region of the first shape model to each corresponding micro region of a second shape model after the deformation, to thereby estimate a shape after the deformation corresponding to the any measurement data.

15. A non-transitory computer readable medium storing a program causing a computer to execute a function comprising:
providing a relation having a feature amount including a difference value between each micro region and another micro region in a first shape model generated from measurement data before deformation as an input, and a displacement from the each micro region of the first shape model to each corresponding micro region of a second shape model after the deformation as an output, and,
when any measurement data is given, computing a displacement corresponding to each micro region of a shape model corresponding to the any measurement data by using the relation, to thereby estimate a shape after the deformation corresponding to the any measurement data.

16. A machine learning device comprising:

a generation unit generating shape models representing individual shapes of a first object and an average shape model based on a plurality of measurement data items of the first object; and a learning unit learning a distribution of a feature amount including a difference value between each micro region constituting the shape model representing the individual shape and each corresponding micro region of the average shape model, and a relation between a distribution of the difference value and a region where a second object having a constraint relation with the first object exists.

17. The machine learning device according to claim 16, wherein the constraint relation includes a relation in which the second object is adjacent to or connected to the first object.

18. A non-transitory computer readable medium storing a program causing a computer to execute:

a function of generating shape models representing individual shapes of a first object and an average shape model based on a plurality of measurement data items of the first object; and a function of learning a distribution of a feature amount including a difference value between each micro region constituting the shape model representing the individual shape and each corresponding micro region of the average shape model, and a relation between a distribution of the difference value and a region where a second object having a constraint relation with the first object exists.

* * * * *